US010196658B2

(12) United States Patent
Dischert et al.

(10) Patent No.: US 10,196,658 B2
(45) **Date of Patent: *Feb. 5, 2019**

(54) MICROORGANISM FOR METHIONINE PRODUCTION WITH IMPROVED METHIONINE SYNTHASE ACTIVITY AND METHIONINE EFFLUX

(71) Applicant: EVONIK DEGUSSA GmbH, Essen (DE)

(72) Inventors: Wanda Dischert, Vic-le-Comte (FR); Perrine Vasseur, Martres-sur-Morges (FR); Rainer Figge, Le Crest (FR)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/915,137

(22) PCT Filed: Sep. 1, 2014

(86) PCT No.: PCT/EP2014/068539

§ 371 (c)(1),
(2) Date: Feb. 26, 2016

(87) PCT Pub. No.: WO2015/028674

PCT Pub. Date: Mar. 5, 2015

(65) Prior Publication Data

US 2016/0177352 A1 Jun. 23, 2016

(30) Foreign Application Priority Data

Aug. 30, 2013 (EP) .................................... 13306185

(51) Int. Cl.

| | |
|---|---|
| ***C12P 13/12*** | (2006.01) |
| ***C12N 15/77*** | (2006.01) |
| ***C12N 15/70*** | (2006.01) |
| ***C07K 14/245*** | (2006.01) |
| ***C07K 14/24*** | (2006.01) |
| ***C07K 14/34*** | (2006.01) |
| ***C12N 9/10*** | (2006.01) |

(52) U.S. Cl.

CPC .............. *C12P 13/12* (2013.01); *C07K 14/24* (2013.01); *C07K 14/245* (2013.01); *C07K 14/34* (2013.01); *C12N 9/1007* (2013.01); *C12N 15/70* (2013.01); *C12N 15/77* (2013.01); *C12Y 201/01013* (2013.01)

(58) Field of Classification Search

CPC ...... C12N 9/1007; C12N 15/70; C12N 15/77; C12P 13/12; C07K 14/24; C07K 14/245; C07K 14/34; C12Y 201/01013

See application file for complete search history.

(56) References Cited

U.S. PATENT DOCUMENTS

2012/0190084 A1 7/2012 Schneider et al.

FOREIGN PATENT DOCUMENTS

| | | |
|---|---|---|
| WO | WO 2006/138689 A2 | 12/2006 |
| WO | WO 2008/127240 A1 | 10/2008 |
| WO | WO 2009/144270 A1 | 12/2009 |

OTHER PUBLICATIONS

Sousa et al., Microbiology 148(Pt5):1291-1303, 2002.*
Witkowski et al., Biochemistry 38:11643-11650, 1999.*
Seffernick et al., J. Bacteriol. 183(8):2405-2410, 2001.*
Branden et al., Introduction to Protein Structure, Garland Publishing Inc., New York, p. 247.*
Sadowski et al., Current Opinion in Structural Biology 19:357-362, 2009.*
Zhou et al., Cell Mol Life Sci 63(19-20):2260-2290, 2006.*
Kozak, M., Gene 234:187-208, 1999.*
Anderson, "Growth Requirements of Virus-Resistant Mutants of *Escherichia coli* Strain "B"," 1946, Bacteriology, Proc. N. A. S., vol. 32, pp. 120-128.
Banerjee et al., "Mechanism of Reductive Activation of Cobalamin-Dependent Methionine Synthase: An Electron Paramagnetic Resonance Spectroelectrochemical Study," 1990, Biochemistry, vol. 29, No. 5, pp. 1129-1135.
Carrier et al., "Library of Synthetic 5' Secondary Structures to Manipulate mRNA Stability in *Escherichia coli*," 1999 (Published on Web Jan. 9, 1999), Biotechnology Progress, vol. 15, No. 1, pp. 58-64 (8 pages).
Datsenko et al., "One-step Inactivation of Chromosomal Genes in *Escherichia coli* K-12 Using PCR Products," Jun. 6, 2000, PNAS, vol. 97, No. 12, pp. 6640-6645.

(Continued)

*Primary Examiner* — Delia M Ramirez
(74) *Attorney, Agent, or Firm* — Birch, Stewart, Kolasch & Birch, LLP

(57) ABSTRACT

The present application is related to a recombinant microorganism optimized for the fermentative production of methionine and/or its derivatives, wherein in said recombinant microorganism, the cobalamin-dependent methionine synthase activity and the methionine efflux are enhanced. The application is also related to a method for optimizing the fermentative production of methionine and/or its derivatives comprising the steps of: c. culturing a recombinant microorganism wherein in said microorganism, the cobalamin-dependent methionine synthase activity and the methionine efflux are enhanced, in an appropriate culture medium comprising a fermentable source of carbon and a source of sulphur, and d. recovering methionine and/or its derivatives from the culture medium.

9 Claims, No Drawings

Specification includes a Sequence Listing.

(56) References Cited

OTHER PUBLICATIONS

Drummond et al., "Characterization of Nonradioactive Assays for Cobalamin-Dependent and Cobalamin-Independent Methionine Synthase Enzymes," 1995, Analytical Biochemistry, vol. 228, No. 2, pp. 323-329.
Eikmanns et al., "A family of Corynebacterium glutamicum/ *Escherichia coli* Shuttle Vectors for Cloning, Controlled Gene Expression, and Promoter Probing," 1991, Gene, vol. 102, pp. 93-98.
European Search Report, dated Dec. 2, 2013, for corresponding European Application No. 13 30 6185.
Foster et al., "The Purification and Properties of a Factor Containing Vitamin $B_{12}$ Concerned in the Synthesis of Methionine by *Escherichia coli*," 1961, Biochemical Journal, vol. 80, pp. 519-531.
Fujii et al., "Activation of Methionine Synthetase by a Reduced Triphosphopyridine Nucleotide-dependent Flavoprotein System," Nov. 10, 1974, Journal of Biological Chemistry, vol. 249, No. 21, pp. 6745-6753.
González et al., "Comparison of Cobalamin-Independent and Cobalamin-Dependent Methionine Synthases from *Escherichia coli*: Two Solutions to the Same Chemical Problem," 1992, Biochemistry, vol. 31, No. 26, pp. 6045-6056.
International Search Report (Form PCT/ISA/210), dated Dec. 1, 2014, for corresponding International Application No. PCT/EP2014/068539.
Lerner et al., "Low Copy Number Plasmids for Regulated Low-level Expression of Cloned Genes in *Escherichia coli* with Blue/White Insert Screening Capability," 1990, Nucleic Acids Research, vol. 18, No. 15, pp. 4631.
Liebl et al., "Requirement of Chelating Compounds for the Growth of Corynebacterium glutamicum in Synthetic Media," 1989, Appl. Microbiol. Biotechnol., vol. 32, pp. 205-210.
Matthews, "Cobalamin-Dependent Methyltransferases," 2001 (published on Web May 24, 2001), Accounts of Chemical Research, vol. 34, No. 8, pp. 681-689.
Riedel et al., "Characterization of the Phosphoenolpyruvate Carboxykinase Gene from Corynebacterium glutamicum and Significance of the Enzyme for Growth and Amino Acid Production," 2001, J. Mol. Microbiol. Biotechnol., vol. 3, No. 4, pp. 573-583.
Saunderson, "Comparative Metabolism of L-methionine, DL-methionine and DL-2-hydroxy 4-methylthiobutanoic Acid by Broiler Chicks." 1985, British Journal of Nutrition, vol. 54, pp. 621-633.
Schaefer et al., "Automated Sampling Device for Monitoring Intracellular Metabolite Dynamics," 1999, Analytical Biochemistry, vol. 270, pp. 88-96.
Trotschel et al., "Characterization of Methionine Export in Corynebacterium glutamicum," Jun. 2005, Journal of Bacteriology, vol. 187, No. 11, pp. 3786-3794.
Wan et al., "Electron Acceptor Specificity of Ferredoxin (Flavodoxin):NADP Oxidoreductase from *Escherichia coli*," 2002, Archives of Biochemistry and Biophysics, vol. 406, pp. 116-126.

* cited by examiner

SEQUENCE LISTING

```
<160> NUMBER OF SEQ ID NOS: 35

<210> SEQ ID NO 1
<211> LENGTH: 245
<212> TYPE: PRT
<213> ORGANISM: Escherichia coli

<400> SEQUENCE: 1

Met Glu Ser Pro Thr Pro Gln Pro Ala Pro Gly Ser Ala Thr Phe Met
1               5                   10                  15

Glu Gly Cys Lys Asp Ser Leu Pro Ile Val Ile Ser Tyr Ile Pro Val
            20                  25                  30

Ala Phe Ala Phe Gly Leu Asn Ala Thr Arg Leu Gly Phe Ser Pro Leu
        35                  40                  45

Glu Ser Val Phe Phe Ser Cys Ile Ile Tyr Ala Gly Ala Ser Gln Phe
    50                  55                  60

Val Ile Thr Ala Met Leu Ala Ala Gly Ser Ser Leu Trp Ile Ala Ala
65                  70                  75                  80

Leu Thr Val Met Ala Met Asp Val Arg His Val Leu Tyr Gly Pro Ser
                85                  90                  95

Leu Arg Ser Arg Ile Ile Gln Arg Leu Gln Lys Ser Lys Thr Ala Leu
            100                 105                 110

Trp Ala Phe Gly Leu Thr Asp Glu Val Phe Ala Ala Ala Thr Ala Lys
        115                 120                 125

Leu Val Arg Asn Asn Arg Arg Trp Ser Glu Asn Trp Met Ile Gly Ile
    130                 135                 140

Ala Phe Ser Ser Trp Ser Ser Trp Val Phe Gly Thr Val Ile Gly Ala
145                 150                 155                 160

Phe Ser Gly Ser Gly Leu Leu Gln Gly Tyr Pro Ala Val Glu Ala Ala
                165                 170                 175

Leu Gly Phe Met Leu Pro Ala Leu Phe Met Ser Phe Leu Leu Ala Ser
            180                 185                 190

Phe Gln Arg Lys Gln Ser Leu Cys Val Thr Ala Ala Leu Val Gly Ala
        195                 200                 205

Leu Ala Gly Val Thr Leu Phe Ser Ile Pro Val Ala Ile Leu Ala Gly
    210                 215                 220

Ile Val Cys Gly Cys Leu Thr Ala Leu Ile Gln Ala Phe Trp Gln Gly
225                 230                 235                 240

Ala Pro Asp Glu Leu
                245


<210> SEQ ID NO 2
<211> LENGTH: 111
<212> TYPE: PRT
<213> ORGANISM: Escherichia coli

<400> SEQUENCE: 2
```

-continued

```
Met Ser Tyr Glu Val Leu Leu Leu Gly Leu Leu Val Gly Val Ala Asn
1               5                   10                  15

Tyr Cys Phe Arg Tyr Leu Pro Leu Arg Leu Arg Val Gly Asn Ala Arg
            20                  25                  30

Pro Thr Lys Arg Gly Ala Val Gly Ile Leu Leu Asp Thr Ile Gly Ile
        35                  40                  45

Ala Ser Ile Cys Ala Leu Leu Val Val Ser Thr Ala Pro Glu Val Met
    50                  55                  60

His Asp Thr Arg Arg Phe Val Pro Thr Leu Val Gly Phe Ala Val Leu
65                  70                  75                  80

Gly Ala Ser Phe Tyr Lys Thr Arg Ser Ile Ile Ile Pro Thr Leu Leu
                85                  90                  95

Ser Ala Leu Ala Tyr Gly Leu Ala Trp Lys Val Met Ala Ile Ile
            100                 105                 110


<210> SEQ ID NO 3
<211> LENGTH: 244
<212> TYPE: PRT
<213> ORGANISM: Citrobacter koseri

<400> SEQUENCE: 3

Met Glu Ser Pro Ala Pro Gln Ser Glu Pro Arg Pro Ala Thr Leu Thr
1               5                   10                  15

Glu Gly Phe Lys Asp Ser Leu Pro Ile Val Ile Ser Tyr Ile Pro Val
            20                  25                  30

Ala Phe Ala Phe Gly Leu Asn Ala Thr Arg Leu Gly Phe Thr Pro Leu
        35                  40                  45

Glu Ser Val Phe Phe Ser Cys Ile Ile Tyr Ala Gly Ala Ser Gln Phe
    50                  55                  60

Val Ile Thr Thr Met Leu Ala Ala Gly Ser Thr Leu Trp Val Ala Ala
65                  70                  75                  80

Leu Thr Val Met Ala Met Asp Val Arg His Val Leu Tyr Gly Pro Ser
                85                  90                  95

Leu Arg Ser Arg Ile Ser Gln Arg Leu Ser Lys Pro Lys Thr Ala Leu
            100                 105                 110

Trp Ala Phe Gly Leu Thr Asp Glu Val Phe Ala Ala Ala Thr Ala Lys
        115                 120                 125

Leu Val Arg Asp Asn Arg Arg Trp Ser Glu Trp Met Ile Gly Ile Ala
    130                 135                 140

Phe Cys Ser Trp Ala Ser Trp Val Leu Gly Thr Val Ile Gly Ala Phe
145                 150                 155                 160

Ser Gly Ser Gly Leu Leu Lys Gly Phe Pro Ala Val Glu Ala Ala Leu
                165                 170                 175

Gly Phe Met Leu Pro Ala Leu Phe Met Ser Phe Leu Leu Ala Ser Phe
            180                 185                 190

Gln Arg Lys Gln Thr Leu Cys Val Thr Ala Ala Leu Ile Gly Ala Leu
        195                 200                 205

Ala Gly Val Thr Leu Phe Ser Ile Pro Ala Ala Ile Leu Ala Gly Ile
    210                 215                 220

Ala Ser Gly Cys Leu Thr Ala Leu Ile Gln Ser Phe Trp Gln Gly Ala
225                 230                 235                 240

Pro Asp Glu Leu


<210> SEQ ID NO 4
```

<211> LENGTH: 111
<212> TYPE: PRT
<213> ORGANISM: Citrobacter koseri

<400> SEQUENCE: 4

```
Met Ser Tyr Glu Val Leu Leu Leu Gly Leu Leu Val Gly Cys Ala Asn
1               5                   10                  15

Tyr Cys Phe Arg Tyr Leu Pro Leu Arg Leu Arg Met Gly Asn Thr Arg
            20                  25                  30

Pro Ala Arg Arg Gly Ala Thr Gly Val Leu Leu Asp Thr Ile Gly Ile
        35                  40                  45

Ala Ser Ile Cys Ala Leu Leu Val Val Ser Thr Ala Pro Glu Val Met
    50                  55                  60

His Asp Ala Ser Arg Phe Ile Pro Thr Leu Val Gly Phe Ala Val Leu
65                  70                  75                  80

Gly Val Ser Phe Tyr Lys Thr Arg Ser Ile Ile Ile Pro Thr Leu Leu
                85                  90                  95

Ser Ala Leu Gly Tyr Gly Leu Ala Trp Lys Ile Glu Val Ile Leu
            100                 105                 110
```

<210> SEQ ID NO 5
<211> LENGTH: 245
<212> TYPE: PRT
<213> ORGANISM: Shigella flexneri

<400> SEQUENCE: 5

```
Met Glu Ser Pro Val Pro Gln Ser Glu Ser Arg Ser Ala Thr Leu Thr
1               5                   10                  15

Glu Gly Phe Lys Asp Ser Leu Pro Ile Val Ile Ser Tyr Ile Pro Val
            20                  25                  30

Ala Phe Ala Phe Gly Met Asn Ala Thr Arg Leu Gly Phe Thr Pro Val
        35                  40                  45

Glu Ser Val Phe Phe Ser Cys Ile Ile Tyr Ala Gly Ala Ser Gln Phe
    50                  55                  60

Val Ile Thr Thr Met Leu Ala Ala Gly Ser Ser Leu Trp Val Ala Ala
65                  70                  75                  80

Leu Thr Val Met Ala Met Asp Val Arg His Val Leu Tyr Gly Pro Ser
                85                  90                  95

Leu Arg Ser Arg Ile Ala Arg Gln Leu Ser Lys Pro Lys Ser Ala Leu
            100                 105                 110

Trp Ala Phe Gly Leu Thr Asp Glu Val Phe Ala Ala Ala Thr Ala Lys
        115                 120                 125

Leu Val Arg Asp Asn Arg Arg Trp Ser Glu Asn Trp Met Ile Gly Ile
    130                 135                 140

Ala Leu Cys Ser Trp Ala Ser Trp Val Leu Gly Thr Val Ile Gly Ala
145                 150                 155                 160

Phe Ser Gly Thr Gly Leu Leu Lys Gly Phe Pro Ala Val Glu Ala Ala
                165                 170                 175

Leu Gly Phe Met Leu Pro Ala Leu Phe Met Ser Phe Leu Leu Ala Ser
            180                 185                 190

Phe Gln Arg Asn Gln Thr Leu Cys Val Thr Ala Ala Leu Ala Gly Ala
        195                 200                 205

Leu Ala Gly Val Thr Leu Phe Ser Ile Pro Ala Ala Ile Leu Ala Gly
    210                 215                 220

Ile Val Cys Gly Cys Leu Thr Ala Leu Ile Gln Ser Phe Trp Gln Gly
225                 230                 235                 240
```

```
Gly Pro Asp Glu Leu
                245


<210> SEQ ID NO 6
<211> LENGTH: 111
<212> TYPE: PRT
<213> ORGANISM: Shigella flexneri

<400> SEQUENCE: 6

Met Ser Tyr Glu Val Leu Leu Leu Gly Leu Leu Val Gly Cys Val Asn
1               5                   10                  15

Tyr Cys Phe Arg Tyr Leu Pro Leu Arg Leu Arg Met Gly Asn Val Arg
            20                  25                  30

Pro Thr Lys Arg Gly Ala Thr Gly Ile Leu Leu Asp Thr Ile Gly Ile
        35                  40                  45

Ala Ser Ile Cys Ala Leu Leu Val Val Ser Thr Ala Pro Glu Val Met
    50                  55                  60

His Asp Ala Arg Arg Phe Val Pro Thr Leu Val Gly Phe Val Val Leu
65                  70                  75                  80

Gly Ala Ser Phe Tyr Lys Thr Arg Ser Ile Ile Ile Pro Thr Leu Leu
                85                  90                  95

Ser Ala Leu Gly Tyr Gly Leu Ala Trp Lys Met Leu Phe Val Leu
            100                 105                 110


<210> SEQ ID NO 7
<211> LENGTH: 242
<212> TYPE: PRT
<213> ORGANISM: Raoultella ornithinolytica

<400> SEQUENCE: 7

Met Glu Lys Pro Ala Pro Ala Ser Glu Ala Thr Leu Pro Glu Gly Ile
1               5                   10                  15

Lys Asp Ser Leu Pro Ile Val Ile Ser Tyr Ile Pro Val Ala Phe Ala
            20                  25                  30

Phe Gly Leu Asn Ala Thr Arg Leu Gly Phe Thr Pro Leu Glu Ser Leu
        35                  40                  45

Phe Phe Ser Cys Ile Ile Tyr Ala Gly Ala Ser Gln Phe Val Ile Thr
    50                  55                  60

Ala Met Leu Ala Ala Gly Ser Ser Leu Trp Val Ala Ala Leu Thr Val
65                  70                  75                  80

Met Ala Met Asp Val Arg His Val Leu Tyr Gly Pro Ser Leu Arg Ser
                85                  90                  95

Arg Ile His Arg Ala Leu Asp Lys Arg Lys Thr Ala Leu Trp Ala Phe
            100                 105                 110

Gly Leu Thr Asp Glu Val Phe Ala Ala Ala Thr Ala Lys Leu Val Arg
        115                 120                 125

Asp Asn Arg Arg Trp Ser Glu Ser Trp Met Leu Gly Ile Ala Phe Thr
    130                 135                 140

Ser Trp Ile Ser Trp Val Phe Gly Thr Leu Ile Gly Ala Tyr Ser Gly
145                 150                 155                 160

Ser Gly Leu Leu Val Gly Phe Pro Ala Val Glu Ala Ala Leu Ser Phe
                165                 170                 175

Met Leu Pro Ala Leu Phe Met Ser Phe Leu Leu Ala Ser Phe Gln Arg
            180                 185                 190

Lys Gln Ser Leu Ser Val Thr Ala Ala Leu Ala Gly Ala Leu Gly Gly
        195                 200                 205
```

```
Ile Ile Leu Phe Ser Ile Pro Ala Ala Ile Leu Ala Gly Ile Val Cys
    210                 215                 220

Gly Cys Leu Ala Ala Leu Ile Gln Ala Ser Ile Gln Gly Met Pro Asp
225                 230                 235                 240

Glu Gln


<210> SEQ ID NO 8
<211> LENGTH: 113
<212> TYPE: PRT
<213> ORGANISM: Raoultella ornithinolytica

<400> SEQUENCE: 8

Met Asn Asn Asn Val Leu Ile Ile Gly Ile Val Val Gly Cys Val Asn
1               5                   10                  15

Tyr Leu Phe Arg Tyr Leu Pro Leu Arg Leu Arg Ala Gly Asn Ala Arg
            20                  25                  30

Pro Thr Arg Arg Gly Pro Leu Ser Val Leu Leu Asp Thr Ile Gly Ile
        35                  40                  45

Ala Ser Ile Cys Ala Leu Leu Ile Val Ser Ser Val Pro Glu Ile Leu
    50                  55                  60

Ser Asp Ser Arg Arg Leu Leu Pro Thr Leu Val Gly Phe Thr Val Leu
65                  70                  75                  80

Gly Leu Ala Phe Trp Lys Thr Arg Ser Ile Ile Met Pro Thr Leu Leu
                85                  90                  95

Ser Ala Leu Ala Tyr Gly Ile Ala Trp Lys Ile Thr Thr Phe Leu Tyr
            100                 105                 110

Phe


<210> SEQ ID NO 9
<211> LENGTH: 250
<212> TYPE: PRT
<213> ORGANISM: Enterobacter sp. (R4-368)

<400> SEQUENCE: 9

Met Asp Met Asp Ser Ser Val Thr Ala Thr Lys Ser Thr Ser Asp Gln
1               5                   10                  15

Ser Ala Thr Phe Leu Glu Gly Ile Lys Asp Ser Leu Pro Ile Val Leu
            20                  25                  30

Ser Tyr Val Pro Val Ala Phe Ala Phe Gly Met Asn Ala Thr Lys Leu
        35                  40                  45

Gly Phe Thr Pro Leu Glu Ser Val Phe Phe Ser Cys Ile Ile Tyr Ala
    50                  55                  60

Gly Ala Ser Gln Phe Val Ile Thr Thr Met Leu Ala Ala Gly Ser Ala
65                  70                  75                  80

Leu Trp Val Ala Ala Leu Thr Val Met Ala Met Asp Val Arg His Val
                85                  90                  95

Leu Tyr Gly Pro Ser Leu Arg Ser Arg Ile Leu Gln Pro Leu Lys Asn
            100                 105                 110

Arg Lys Thr Ala Val Trp Ala Phe Gly Leu Thr Asp Glu Val Phe Ala
        115                 120                 125

Ala Ala Thr Ala Lys Leu Val Arg Asp Asn Arg Arg Trp Ser Glu Asn
    130                 135                 140

Trp Met Ile Gly Ile Ala Leu Phe Ser Trp Leu Ser Trp Val Ala Gly
145                 150                 155                 160

Thr Val Leu Gly Ala Phe Ser Gly Asp Gly Leu Leu Asp Gly Tyr Pro
```

```
                165                 170                 175

Ala Val Glu Ser Ala Leu Gly Phe Met Leu Pro Ala Leu Phe Met Ser
            180                 185                 190

Phe Leu Leu Ala Ser Phe Gln Arg Arg Gln Ile Ser Ala Val Thr Ala
        195                 200                 205

Ala Leu Leu Gly Ala Leu Ala Gly Val Thr Leu Phe Ser Ile Pro Ala
    210                 215                 220

Ala Ile Leu Ala Gly Ile Phe Ala Gly Cys Leu Ala Ala Leu Val Gln
225                 230                 235                 240

Ala Phe Tyr Gln Gly Ala Ser Asp Ala Gln
                245                 250


<210> SEQ ID NO 10
<211> LENGTH: 111
<212> TYPE: PRT
<213> ORGANISM: Enterobacter sp. (R4-368)

<400> SEQUENCE: 10

Met Arg Asn Glu Val Leu Leu Leu Gly Leu Leu Val Gly Cys Val Asn
1               5                   10                  15

Phe Leu Phe Arg Tyr Leu Pro Leu Arg Ile Arg Ala Gly Gln Ser Arg
            20                  25                  30

Pro Ala Lys Arg Gly Val Ser Gly Val Phe Leu Asp Thr Ile Gly Ile
        35                  40                  45

Ala Ser Ile Cys Ala Leu Leu Val Val Ser Cys Val Pro Glu Ile Ala
    50                  55                  60

Ala Asp Ser Arg Arg Leu Leu Pro Thr Leu Ala Gly Phe Ala Val Leu
65                  70                  75                  80

Gly Val Ser Phe Trp Lys Thr Arg Ser Ile Ile Leu Pro Thr Leu Leu
                85                  90                  95

Ser Ala Phe Ala Tyr Gly Ile Val Trp Lys Leu Leu Ala Asp Ala
            100                 105                 110


<210> SEQ ID NO 11
<211> LENGTH: 257
<212> TYPE: PRT
<213> ORGANISM: Yersinia enterocolitica subsp. enterocolitica

<400> SEQUENCE: 11

Met Gln Ser Gln Thr Thr Asp Ser Pro Ser Thr Ala Gln Pro Thr Ala
1               5                   10                  15

Thr Phe Ile Glu Gly Ile Thr Asp Ser Leu Pro Ile Val Ile Gly Tyr
            20                  25                  30

Leu Pro Val Ala Phe Ala Phe Gly Leu Ser Ser Val Lys Leu Gly Phe
        35                  40                  45

Thr Pro Trp Glu Ala Ile Phe Phe Ser Cys Ile Ile Tyr Ala Gly Ala
    50                  55                  60

Ser Gln Phe Val Ile Thr Ala Leu Leu Ser Ala Gly Met Ser Leu Trp
65                  70                  75                  80

Val Ser Ala Leu Thr Val Met Ala Met Asp Val Arg His Ile Leu Tyr
                85                  90                  95

Gly Pro Ala Leu Lys His Arg Ile Val Thr Arg Leu Ser Gly Lys Lys
            100                 105                 110

Thr Ala Leu Trp Ala Phe Gly Leu Thr Asp Glu Val Phe Ala Ala Ala
        115                 120                 125

Thr Thr Lys Leu Met Lys Asp Gln Arg Arg Trp Ser Glu Asn Trp Met
```

```
    130                 135                 140

Leu Gly Ile Ala Phe Thr Ser Trp Leu Ser Trp Val Ala Gly Thr Ala
145                 150                 155                 160

Ile Gly Ala Met Phe Gly His Gly Pro Leu Glu Asn Tyr Pro Ala Ile
                165                 170                 175

Glu Ala Ser Leu Ser Phe Met Leu Pro Ala Leu Phe Leu Ser Phe Leu
            180                 185                 190

Leu Ala Ser Phe Lys Arg Gln Tyr Ser Leu Thr Val Ile Ala Ser Leu
        195                 200                 205

Thr Gly Ala Leu Leu Gly Val Leu Leu Phe Ser Ile Pro Val Ala Ile
    210                 215                 220

Leu Ala Gly Ile Gly Gly Gly Cys Leu Ala Ala Leu Leu Gln Pro Val
225                 230                 235                 240

Pro Glu Thr Val Ile Glu Asn Asn Glu Ser Asp Lys Glu Glu Pro Lys
                245                 250                 255

Pro


<210> SEQ ID NO 12
<211> LENGTH: 257
<212> TYPE: PRT
<213> ORGANISM: Yersinia enterocolitica subsp. enterocolitica

<400> SEQUENCE: 12

Met Gln Ser Gln Thr Thr Asp Ser Pro Ser Thr Ala Gln Pro Thr Ala
1               5                   10                  15

Thr Phe Ile Glu Gly Ile Thr Asp Ser Leu Pro Ile Val Ile Gly Tyr
            20                  25                  30

Leu Pro Val Ala Phe Ala Phe Gly Leu Ser Ser Val Lys Leu Gly Phe
        35                  40                  45

Thr Pro Trp Glu Ala Ile Phe Phe Ser Cys Ile Ile Tyr Ala Gly Ala
    50                  55                  60

Ser Gln Phe Val Ile Thr Ala Leu Leu Ser Ala Gly Met Ser Leu Trp
65                  70                  75                  80

Val Ser Ala Leu Thr Val Met Ala Met Asp Val Arg His Ile Leu Tyr
                85                  90                  95

Gly Pro Ala Leu Lys His Arg Ile Val Thr Arg Leu Ser Gly Lys Lys
            100                 105                 110

Thr Ala Leu Trp Ala Phe Gly Leu Thr Asp Glu Val Phe Ala Ala Ala
        115                 120                 125

Thr Thr Lys Leu Met Lys Asp Gln Arg Arg Trp Ser Glu Asn Trp Met
    130                 135                 140

Leu Gly Ile Ala Phe Thr Ser Trp Leu Ser Trp Val Ala Gly Thr Ala
145                 150                 155                 160

Ile Gly Ala Met Phe Gly His Gly Pro Leu Glu Asn Tyr Pro Ala Ile
                165                 170                 175

Glu Ala Ser Leu Ser Phe Met Leu Pro Ala Leu Phe Leu Ser Phe Leu
            180                 185                 190

Leu Ala Ser Phe Lys Arg Gln Tyr Ser Leu Thr Val Ile Ala Ser Leu
        195                 200                 205

Thr Gly Ala Leu Leu Gly Val Leu Leu Phe Ser Ile Pro Val Ala Ile
    210                 215                 220

Leu Ala Gly Ile Gly Gly Gly Cys Leu Ala Ala Leu Leu Gln Pro Val
225                 230                 235                 240

Pro Glu Thr Val Ile Glu Asn Asn Glu Ser Asp Lys Glu Glu Pro Lys
```

245 250 255

Pro

<210> SEQ ID NO 13
<211> LENGTH: 113
<212> TYPE: PRT
<213> ORGANISM: Yersinia enterocolitica subsp. enterocolitica

<400> SEQUENCE: 13

Met Asn Met Asp Val Val Ile Ile Gly Leu Val Val Gly Thr Val Asn
1 5 10 15

Tyr Leu Phe Arg Tyr Leu Pro Leu Arg Leu Gly Pro Ala Arg Lys Gln
20 25 30

Ala Gly Leu Gln Arg Gly Lys Val Ser Leu Leu Leu Asp Ser Ile Gly
35 40 45

Ile Ala Ser Ile Cys Ala Leu Leu Val Val Ser Ser Thr Pro Glu Ile
50 55 60

Val His Thr Pro Gln Lys Leu Ile Pro Thr Leu Ile Gly Phe Leu Val
65 70 75 80

Ile Cys Gly Cys Phe Tyr Lys Thr Asn Ser Ile Ile Phe Ala Thr Leu
85 90 95

Leu Gly Ala Leu Ser Tyr Gly Leu Thr Phe Lys Leu Leu Met Ile Leu
100 105 110

Ala

<210> SEQ ID NO 14
<211> LENGTH: 113
<212> TYPE: PRT
<213> ORGANISM: Yersinia enterocolitica subsp. enterocolitica

<400> SEQUENCE: 14

Met Asn Met Asp Val Val Ile Ile Gly Leu Val Val Gly Thr Val Asn
1 5 10 15

Tyr Leu Phe Arg Tyr Leu Pro Leu Arg Leu Gly Pro Ala Arg Lys Gln
20 25 30

Ala Gly Leu Gln Arg Gly Lys Val Ser Leu Leu Leu Asp Ser Ile Gly
35 40 45

Ile Ala Ser Ile Cys Ala Leu Leu Val Val Ser Ser Thr Pro Glu Ile
50 55 60

Val His Asn Pro Gln Lys Leu Ile Pro Thr Leu Ile Gly Phe Leu Val
65 70 75 80

Ile Cys Gly Cys Phe Tyr Lys Thr Asn Ser Ile Ile Phe Ala Thr Leu
85 90 95

Leu Gly Ala Leu Ser Tyr Gly Leu Thr Phe Lys Leu Leu Met Ile Leu
100 105 110

Ala

<210> SEQ ID NO 15
<211> LENGTH: 252
<212> TYPE: PRT
<213> ORGANISM: Photorhabdus luminescens subsp. laumondii

<400> SEQUENCE: 15

Met Pro Val Ser Asp Thr Ser Ser Pro Leu Thr Ser Lys Lys Ser Ser
1 5 10 15

Phe Thr Glu Gly Ile Ile Asp Ser Leu Pro Ile Val Ile Gly Tyr Ile
20 25 30

```
Pro Val Ala Phe Ala Phe Gly Leu Asn Ala Val Lys Leu Gly Phe Asn
        35                  40                  45

Pro Met Glu Ala Ile Phe Phe Ser Cys Ile Ile Tyr Ala Gly Ala Ser
    50                  55                  60

Gln Phe Val Ile Thr Ala Leu Leu Ser Ala Gly Thr Ser Leu Trp Ile
65                  70                  75                  80

Ser Ala Leu Thr Ile Met Ala Met Asp Val Arg His Ile Leu Tyr Gly
                85                  90                  95

Pro Ser Leu Arg His Arg Ile Lys Asp Lys Leu Thr Glu Lys Lys Thr
            100                 105                 110

Val Ile Trp Ala Phe Gly Leu Thr Asp Glu Val Phe Ala Ala Ala Thr
        115                 120                 125

Ala Lys Leu Ile Lys Asn His Arg Ser Trp Ser Glu Asn Trp Met Val
    130                 135                 140

Ala Ile Ala Ile Cys Ser Trp Leu Ala Trp Gly Ala Gly Thr Ala Ala
145                 150                 155                 160

Gly Ala Phe Leu Gly Asn Gly Tyr Leu Glu Ser Tyr Pro Ala Ile Glu
                165                 170                 175

Ala Ala Met Ile Phe Met Leu Pro Ala Leu Phe Leu Ser Phe Leu Leu
            180                 185                 190

Ala Ser Cys Arg Lys Gln Asn Ser Tyr Cys Val Ala Thr Ala Leu Thr
        195                 200                 205

Gly Ala Leu Leu Gly Ile Thr Phe Phe Ser Ile Pro Val Ala Ile Leu
    210                 215                 220

Ala Gly Ile Val Gly Gly Cys Ile Ala Ala Leu Leu Gln Pro Gln Asn
225                 230                 235                 240

Asn Cys Asn Asp Ser Ser Glu Gln Lys Glu Thr Pro
                245                 250


<210> SEQ ID NO 16
<211> LENGTH: 112
<212> TYPE: PRT
<213> ORGANISM: Photorhabdus luminescens subsp. laumondii

<400> SEQUENCE: 16

Met Ile Asp Ser Lys Ile Leu Leu Ile Gly Leu Phe Val Gly Leu Ala
1               5                   10                  15

Asn Phe Ser Phe Arg Tyr Leu Pro Leu Arg Phe Gly Lys Ala Arg Gln
            20                  25                  30

Ser Ala Gly Arg Lys Ala Gly Lys Thr Ser Ile Ile Leu Asp Ser Ile
        35                  40                  45

Gly Ile Ala Ser Ile Cys Ser Leu Leu Ile Val Ser Gly Val Pro Asp
    50                  55                  60

Val Met Arg Glu Ser Gln Lys Leu Leu Pro Thr Leu Ile Gly Cys Leu
65                  70                  75                  80

Thr Ile Cys Leu Val Phe Tyr Lys Thr Lys Gln Ile Ile Leu Ala Thr
                85                  90                  95

Leu Phe Gly Ala Leu Leu Phe Gly Leu Thr Phe Lys Ile Phe Met Asn
            100                 105                 110


<210> SEQ ID NO 17
<211> LENGTH: 245
<212> TYPE: PRT
<213> ORGANISM: Citrobacter youngae

<400> SEQUENCE: 17
```

```
Met Asp Ser Pro Ile Pro Gln Ser Gly Ser Arg Ser Ala Thr Leu Thr
1               5                   10                  15

Glu Gly Phe Lys Asp Ser Leu Pro Ile Val Ile Ser Tyr Ile Pro Val
            20                  25                  30

Ala Phe Ala Phe Gly Leu Asn Ala Thr Arg Leu Gly Phe Thr Pro Val
        35                  40                  45

Glu Ser Val Phe Leu Ser Cys Ile Ile Tyr Ala Gly Ala Ser Gln Phe
    50                  55                  60

Val Ile Thr Thr Met Leu Ala Ala Gly Ser Ser Leu Trp Val Ala Ala
65                  70                  75                  80

Leu Thr Val Met Ala Met Asp Val Arg His Val Leu Tyr Gly Pro Ser
                85                  90                  95

Leu Arg Ser Arg Ile Ala Gln Arg Leu Ser Lys Pro Lys Ser Ala Leu
            100                 105                 110

Trp Ala Phe Gly Leu Thr Asp Glu Val Phe Ala Ala Ala Thr Ala Lys
        115                 120                 125

Leu Val Arg Asp Asn Arg Arg Trp Ser Glu Asn Trp Met Ile Gly Ile
    130                 135                 140

Ala Leu Cys Ser Trp Ala Ser Trp Val Phe Gly Thr Ala Ile Gly Ala
145                 150                 155                 160

Phe Ser Gly Ser Gly Leu Leu Lys Asp Tyr Pro Ala Val Glu Ala Ala
                165                 170                 175

Leu Gly Phe Met Leu Pro Ala Leu Phe Met Ser Phe Leu Leu Ala Ser
            180                 185                 190

Phe Gln Arg Lys Gln Ala Leu Cys Val Thr Val Ala Leu Thr Gly Ala
        195                 200                 205

Leu Ala Gly Val Ile Leu Phe Ser Ile Pro Ala Ala Ile Leu Leu Gly
    210                 215                 220

Ile Val Cys Gly Cys Leu Thr Ala Leu Leu Gln Ser Phe Trp Gln Gly
225                 230                 235                 240

Gly Pro Asp Glu Leu
                245
```

<210> SEQ ID NO 18
<211> LENGTH: 111
<212> TYPE: PRT
<213> ORGANISM: Citrobacter youngae

<400> SEQUENCE: 18

```
Met Ser Tyr Glu Val Leu Leu Leu Gly Leu Leu Val Gly Cys Val Asn
1               5                   10                  15

Tyr Cys Phe Arg Tyr Leu Pro Leu Arg Leu Gly Ala Gly Asn Val Arg
            20                  25                  30

Pro Ala Arg Arg Gly Ala Thr Gly Ile Leu Leu Asp Thr Ile Gly Ile
        35                  40                  45

Ala Ser Ile Cys Ala Leu Leu Val Val Ser Thr Ala Pro Glu Val Met
    50                  55                  60

His Asp Ala Arg Arg Phe Val Pro Thr Leu Val Gly Phe Val Ile Leu
65                  70                  75                  80

Gly Ala Ser Phe Tyr Lys Thr Arg Ser Ile Ile Ile Pro Thr Leu Leu
                85                  90                  95

Ser Ala Leu Gly Tyr Gly Leu Ala Trp Lys Met Leu Val Gly Leu
            100                 105                 110
```

-continued

<210> SEQ ID NO 19
<211> LENGTH: 245
<212> TYPE: PRT
<213> ORGANISM: Citrobacter freundii

<400> SEQUENCE: 19

```
Met Glu Ser Pro Val Pro Gln Ser Glu Ser Ser Ser Ala Thr Leu Thr
1               5                   10                  15

Glu Gly Phe Lys Asp Ser Leu Pro Ile Val Ile Ser Tyr Ile Pro Val
            20                  25                  30

Ala Phe Ala Phe Gly Leu Asn Ala Thr Arg Leu Gly Phe Thr Pro Val
        35                  40                  45

Glu Ser Val Phe Phe Ser Cys Ile Ile Tyr Ala Gly Ala Ser Gln Phe
    50                  55                  60

Val Ile Thr Thr Met Leu Ala Ala Gly Ser Ser Leu Trp Val Ala Ala
65                  70                  75                  80

Leu Thr Val Met Ala Met Asp Val Arg His Val Leu Tyr Gly Pro Ser
                85                  90                  95

Leu Arg Ser Arg Ile Ala Gln Arg Leu Ser Lys Pro Lys Ser Ala Leu
            100                 105                 110

Trp Ala Phe Gly Leu Thr Asp Glu Val Phe Ala Ala Ala Thr Ala Lys
        115                 120                 125

Leu Val Arg Asp Asn Arg Arg Trp Ser Glu Asn Trp Met Ile Gly Ile
    130                 135                 140

Ala Leu Cys Ser Trp Ala Ser Trp Val Phe Gly Thr Val Leu Gly Ala
145                 150                 155                 160

Phe Ser Gly Ser Gly Leu Leu Lys Asp Tyr Pro Ala Val Glu Ala Ala
                165                 170                 175

Leu Gly Phe Met Leu Pro Ala Leu Phe Met Ser Phe Leu Leu Ala Ser
            180                 185                 190

Phe Gln Arg Lys Gln Ala Leu Cys Val Thr Ala Ala Leu Ala Gly Ala
        195                 200                 205

Leu Ala Gly Val Met Leu Phe Ser Ile Pro Ala Ala Ile Leu Ala Gly
    210                 215                 220

Ile Val Cys Gly Cys Leu Thr Ala Leu Ile Gln Ser Phe Trp Gln Gly
225                 230                 235                 240

Gly Pro Asp Glu Leu
                245
```

<210> SEQ ID NO 20
<211> LENGTH: 111
<212> TYPE: PRT
<213> ORGANISM: Citrobacter freundii

<400> SEQUENCE: 20

```
Met Ser Tyr Glu Val Leu Leu Leu Gly Leu Leu Val Gly Cys Val Asn
1               5                   10                  15

Tyr Cys Phe Arg Tyr Leu Pro Leu Arg Leu Gly Val Gly Asn Val Arg
            20                  25                  30

Pro Thr Lys Arg Gly Ala Thr Gly Ile Leu Leu Asp Thr Ile Gly Ile
        35                  40                  45

Thr Ser Ile Cys Ala Leu Leu Val Val Ser Thr Ala Pro Glu Val Met
    50                  55                  60

His Asp Ala Arg Arg Phe Val Pro Thr Leu Val Gly Phe Val Ile Leu
65                  70                  75                  80

Gly Ala Ser Phe Tyr Lys Thr Arg Ser Ile Ile Ile Pro Thr Leu Leu
```

85 90 95

Ser Ala Leu Gly Tyr Gly Leu Ala Trp Lys Met Leu Val Val Leu
100 105 110

<210> SEQ ID NO 21
<211> LENGTH: 100
<212> TYPE: DNA
<213> ORGANISM: Artificial Sequence
<220> FEATURE:
<223> OTHER INFORMATION: Oligonucleotide

<400> SEQUENCE: 21
aacactgcaa aatcctgcta tttgatttgt atgagtgata agtgtaacgc cgaataatcg 60
tcgttggcga attttacgac tctgacagga ggtggcaatg 100

<210> SEQ ID NO 22
<211> LENGTH: 100
<212> TYPE: DNA
<213> ORGANISM: Artificial Sequence
<220> FEATURE:
<223> OTHER INFORMATION: Oligonucleotide

<400> SEQUENCE: 22
gagaaagtaa acgtaacatg atgacgacaa ttctgacgat tcatgttcct tcaacgccgg 60
ggcgcgcatg gaatatgctg gtggcacttc aggcaggaaa 100

<210> SEQ ID NO 23
<211> LENGTH: 100
<212> TYPE: DNA
<213> ORGANISM: Artificial Sequence
<220> FEATURE:
<223> OTHER INFORMATION: Oligonucleotide

<400> SEQUENCE: 23
tgaggaatag acaatgttag ttagtaaaag caacggattt aacgctagcg cagttttggg 60
tagtggaagt tataatgaaa ataaatcttc taaacacatg 100

<210> SEQ ID NO 24
<211> LENGTH: 100
<212> TYPE: DNA
<213> ORGANISM: Artificial Sequence
<220> FEATURE:
<223> OTHER INFORMATION: Oligonucleotide

<400> SEQUENCE: 24
tgcgctaaaa gaaatgaata gaaccttttc gataatataa gaaaaagtga ttttcatgtt 60
ggtttactta agccaagtag tacgcgtagt gttattttag 100

<210> SEQ ID NO 25
<211> LENGTH: 45
<212> TYPE: DNA
<213> ORGANISM: Artificial Sequence
<220> FEATURE:
<223> OTHER INFORMATION: Oligonucleotide

<400> SEQUENCE: 25
aaattattct tgtatctttg ttataatatg ggaaagtgca accat 45

<210> SEQ ID NO 26
<211> LENGTH: 100
<212> TYPE: DNA
<213> ORGANISM: Artificial Sequence
<220> FEATURE:

-continued

<223> OTHER INFORMATION: Oligonucleotide

<400> SEQUENCE: 26
cgttaatcag caggttagcc agccacaaaa agccattgag aaaattattg attttacatg 60
ggattattat attgctaatc cttggttttt aaaaattgtg 100

<210> SEQ ID NO 27
<211> LENGTH: 100
<212> TYPE: DNA
<213> ORGANISM: Artificial Sequence
<220> FEATURE:
<223> OTHER INFORMATION: Oligonucleotide

<400> SEQUENCE: 27
tcatctaccg cgcacgaata aaactgccat ccggctggcg ggtgaacagg acctgttgat 60
tattccccgt atcaatggtt aagcccgtca ccacgccgct 100

<210> SEQ ID NO 28
<211> LENGTH: 1063
<212> TYPE: DNA
<213> ORGANISM: Citrobacter koseri

<400> SEQUENCE: 28
atggaaagcc ctgcacccca gtctgagccc cgtccggcaa cattaacgga aggattcaaa 60
gacagtttac cgatagtcat aagttatatt ccggtggcgt ttgcgtttgg ccttaacgcc 120
acccgtctgg gctttactcc cctcgaaagc gttttttttct cctgcattat ttacgcaggc 180
gccagccagt tcgtcatcac caccatgctc gcggcgggca gcacattatg ggtcgccgcg 240
ctgaccgtga tggcgatgga cgtgcgtcat gtgctgtacg gcccttccct gcgtagtcgc 300
atcagccaac ggctcagtaa acctaaaacc gccctgtggg catttggcct caccgatgaa 360
gtgtttgctg ccgccacggc caaactggtg cgggataacc gccgctggag tgaaaactgg 420
atgatcggca tcgcgttctg ctcctgggcc tcctgggtgc tcggcacggt cattggcgca 480
ttttccggga gcggattgct gaaaggcttc cccgccgttg aggcggcatt aggttttatg 540
ctgccagccc tgtttatgag ctttttgctc gcttcttttc aacgcaaaca aacgctgtgc 600
gtcacggcgg cgttaatcgg cgcgctggca ggcgtcacgc tgttttccat tcctgcggct 660
atcctggcgg gtatcgccag cgggtgtctg accgccttga tccagtcgtt ctggcaagga 720
gcgcccgatg agttatgagg ttctgctgct gggactgctg gtcggctgcg ccaattattg 780
ttttcgttat ttaccgcttc gtctgcgaat gggaaacacc cgccccgcca ggcgcggcgc 840
aacgggcgtg ttgctcgaca ccattggcat cgcgtccatc tgcgccctgc tggtggtgtc 900
tacggctccc gaagtgatgc acgacgccag ccggttcatt ccgacgctgg tcgggtttgc 960
cgtcctgggc gtcagtttct acaagacgcg cagcatcatc atcccaacgc tactgagcgc 1020
tctgggctat ggactcgcct ggaagataga ggtcatttta taa 1063

<210> SEQ ID NO 29
<211> LENGTH: 1063
<212> TYPE: DNA
<213> ORGANISM: Shigella flexneri

<400> SEQUENCE: 29
atggaaagcc ctgttcccca gtctgaatcc cgttctgcaa cgttaactga aggattcaaa 60
gacagcctac cgatagttat cagttatatt ccggtcgcat ttgcatttgg tatgaatgcg 120
actcgcctgg gctttactcc cgttgaaagc gttttttttct cctgcatcat ttacgctggc 180

```
gccagccagt ttgtcatcac aaccatgctc gccgcaggca gctcactgtg ggtcgcggct    240

ctgaccgtca tggcgatgga tgttcgccat gttttgtacg gcccttctct gcgcagccgt    300

atcgcccgac agctgagcaa acctaaaagc gcgctatggg cctttggcct caccgacgaa    360

gtctttgccg cggcaacggc caagctggtg cgggataacc ggcgctggag tgaaaactgg    420

atgatcggca tcgcgctatg ctcctgggct tcctgggtac ttggtacggt tatcggcgca    480

ttttccggca ctggcttact gaagggattc ccggcggtag aagcggcgct ggggtttatg    540

ctcccggcgc tgtttatgag ttttctgctg gcctctttcc agcgtaatca aacgctatgc    600

gtcacggcgg ctttagccgg tgcgctggct ggcgtgacgc tgttttctat cccggcagcc    660

atcctcgcag gcatagtctg cggatgcctg accgcgctca ttcagtcgtt ctggcaggga    720

ggtcctgatg agttatgagg ttctgctgct cggcctgctg gtcggctgcg tcaattactg    780

ttttcgctat ttaccactgc gtctgcgaat ggggaatgtg cgcccgacaa aacgcggagc    840

cactggaata ctactcgaca ccatcggtat tgcatcaatt tgcgccctgc tagtggtgtc    900

tactgcgcca gaagtgatgc acgatgcccg tcgttttgtg cctacgctgg tggggtttgt    960

ggtactgggt gcaagcttct ataagacccg cagcatcatc attccgacct tactgagtgc   1020

cctgggctat ggattagcct ggaaaatgct gtttgtctta tag                     1063
```

<210> SEQ ID NO 30
<211> LENGTH: 1060
<212> TYPE: DNA
<213> ORGANISM: Raoultella ornithinolytica

<400> SEQUENCE: 30

```
atggaaaaac cggcaccggc aagcgaagca accctgccgg aaggtattaa agatagcctg     60

ccgattgtga ttagctatat tccggttgca tttgcctttg gtctgaatgc aacccgtctg    120

ggttttacac cgctggaaag cctgtttttt agctgtatta tctatgccgg tgcaagccag    180

tttgttatta ccgcaatgct ggcagcaggt agcagcctgt gggttgcagc actgaccgtt    240

atggcaatgg atgttcgtca tgttctgtat ggtccgagcc tgcgtagccg tattcatcgt    300

gcactggata aacgtaaaac cgcactgtgg gcatttggcc tgaccgatga agtttttgca    360

gcagcaaccg caaaactggt tcgtgataat cgtcgttgga gcgaaagctg gatgctgggt    420

attgcattta ccagctggat tagctgggtt tttggcaccc tgattggtgc atatagcggt    480

agcggtctgc tggttggttt tccggcagtt gaagcagccc tgagctttat gctgcctgca    540

ctgtttatga gttttctgct ggcaagcttt cagcgtaaac agagcctgag cgttaccgca    600

gcactggcag gcgcactggg tggtattatt ctgtttagca ttccggcagc aattctggca    660

ggtattgttt gtggttgtct ggcagcgctg attcaggcaa gcattcaggg tatgccggat    720

gaacaataac gttctgatta ttggtattgt ggtgggctgt gtgaattacc tgtttcgtta    780

tctgccgctg cgtctgcgtg caggtaatgc acgtccgacc cgtcgtggtc cgctgagcgt    840

tctgctggat accattggca ttgcaagcat ttgtgcactg ctgattgtta gcagcgttcc    900

ggaaattctg agcgatagcc gtcgtctgct gccgaccctg gttggtttta ccgttctggg    960

tctggcattt tggaaaaccc gtagcattat tatgccgaca ctgctgagcg cactggccta   1020

tggtattgca tggaaaatta ccacctttct gtatttttga                         1060
```

<210> SEQ ID NO 31
<211> LENGTH: 1078
<212> TYPE: DNA

<213> ORGANISM: Enterobacter sp. (R4-368)

<400> SEQUENCE: 31
atggatatgg atagcagcgt taccgcaacc aaaagcacca gcgatcagag cgcaaccttt 60
ctggaaggta ttaaagatag cctgccgatt gttctgagct atgttccggt tgcatttgcc 120
tttggtatga atgcaaccaa actgggtttt acaccgctgg aaagcgtgtt ttttagctgt 180
attatctatg ccggtgcaag ccagtttgtt attaccacca tgctggcagc aggtagcgca 240
ctgtgggttg cagcactgac cgttatggca atggatgttc gtcatgttct gtatggtccg 300
agcctgcgta gccgtattct gcagccgctg aaaaatcgta aaaccgcagt gtgggcattt 360
ggtctgaccg atgaagtttt tgcagcagca accgcaaaac tggttcgtga taatcgtcgt 420
tggagcgaaa attggatgat tggtattgca ctgtttagct ggctgagctg ggttgccggt 480
acagttctgg gtgcatttag cggtgatggt ctgctggatg gttatccggc agttgaaagt 540
gcactgggct ttatgctgcc tgccctgttt atgagctttc tgctggcaag ctttcagcgt 600
cgtcagatta gcgcagttac cgcagcactg ctgggtgcac tggcaggcgt taccctgttt 660
agcattccgg cagcaattct ggcaggcatt tttgcaggtt gtctggcagc actggttcag 720 gcctttttatc agggtgcaag tgatgcgcaa tgaggttctg ctgctgggcc tgctggttgg 780
ttgtgttaat ttctgtttc gttatctgcc gctgcgtatt cgtgcaggtc agagccgtcc 840
ggcaaaacgt ggtgttagcg gtgtttttct ggataccatt ggcattgcaa gcatttgtgc 900
cctgctggta gttagctgtg ttccggaaat tgcagcagat agccgtcgtc tgctgccgac 960
cctggcaggt tttgcagtgc tggtgttag cttttggaaa acccgtagca ttattctgcc 1020
gacactgctg agcgcatttg cgtatggtat tgtttggaaa ctgctggcag atgcctaa 1078

<210> SEQ ID NO 32
<211> LENGTH: 1112
<212> TYPE: DNA
<213> ORGANISM: Yersinia enterocolitica subsp. enterocolitica

<400> SEQUENCE: 32
atgcaaagcc aaaccaccga ctccccctcg acggcccagc cgaccgccac ctttattgaa 60
ggaataaccg atagcctacc gattgttatc ggttatctac ccgttgcttt tgcctttggt 120
ttgagttcgg taaaacttgg ctttactccg tgggaagcta ttttcttttc ttgcattatt 180
tatgccggag ccagccaatt cgttattacc gccctgctca gcgcggggat gtcattgtgg 240
gtttccgcct tgaccgtgat ggctatggat gtccgccata tcttgtacgg gccagcactg 300
aaacaccgca ttgtaaccag gttatctggc aaaaaaacgg cgctgtgggc ctttggtctt 360
actgatgaag tgtttgccgc cgcaacaacc aagctaatga aagatcaacg gcgctggagt 420
gaaaactgga tgcttggcat cgcgttcacc tcttggttgt cttgggtagc tggcaccgct 480
atcggcgcga tgtttggtca tggccgctg gaaaattacc cggcgattga agcatcactc 540
tcctttatgc tcccggcgct attcctcagc ttcttattgg cctcgttcaa acgccaatac 600
agccttaccg ttattgcttc actgaccgga gccttgctgg gcgtgctgct gttctctatt 660
ccggtggcta ttttagccgg tattggcggc ggatgcctgg cagccctgct ccaacccgtc 720
cccgagaccg ttatagaaaa taacgagagt gataaagagg agccgaagcc atgaatatgg 780
atgttgtgat cattggtttg gtggtgggaa cggtcaatta cctgtttcgt tatctgccgc 840
tgcgcctggg gcctgcccgt aaacaagcag gcctgcaacg agggaaagtc tccctgttgc 900
tagacagcat cgggatcgcc tctatctgtg cgttgttggt ggtttccagt accccggaga 960
tagtgcataa cccacagaaa ttaattccta cactaattgg ttttttagtt atctgtggat 1020
gcttttataa aaccaacagt attatcttcg ccaccttact gggagcactc agttacggtc 1080
tgacattcaa attactgatg attttggcat aa 1112

<210> SEQ ID NO 33
<211> LENGTH: 1094
<212> TYPE: DNA
<213> ORGANISM: Photorhabdus luminescens subsp. laumondii

<400> SEQUENCE: 33
atgcctgttt ctgatacatc atccccctta acgagtaaaa aatcttcttt tactgaagga 60
ataatagata gtttacccat tgttatcggt tatattcccg tcgcctttgc ttttggtctc 120
aatgccgtca aacttggctt caacccaatg gaagccattt tcttttcatg catcatctac 180
gccggtgcaa gccagttcgt catcacagct ttactgagtg cggggacatc attatggatt 240
tctgccctaa caattatggc aatggatgtc cgccatattc tttatggtcc atctttaagg 300
caccgtatca aagataagct aacggagaaa aaaaccgtta tctgggcttt cggcctgaca 360
gatgaagttt ttgccgccgc gactgcaaaa ctcattaaaa accaccggag ctggagtgaa 420
aactggatgg ttgctattgc aatctgttct tggctggcct ggggcgcagg taccgcagcc 480
ggtgcatttc ttggtaacgg ttatttggaa tcctatcccg ctatagaagc tgccatgatt 540
ttcatgttac cagcactatt tctcagtttt cttcttgctt cttgtagaaa acaaaatagt 600
tattgtgttg caaccgcact aaccggagca cttttaggga ttacattttt ctcaattcca 660
gttgctattc tggcaggtat tgtcggtggt tgtatcgcgg cactgttaca accgcaaaac 720
aattgcaatg actcttcaga acaaaaggaa acaccatgat tgatagcaag attttgctga 780
ttggactatt tgttgggtta gctaactttt catttcgcta tctgccacta cgatttggga 840
aagcacgcca atctgccggc agaaaagctg gaaaaacaag cattatcctt gacagtattg 900
gtattgcatc catttgttct ttactcatcg tatcaggtgt acctgatgtg atgagagaaa 960
gtcaaaaact acttcctacc ctcataggtt gtctgaccat ctgtttagtc ttttacaaaa 1020
caaagcaaat tatactcgca acactatttg gcgcactgct tttggacta acattcaaaa 1080 tatttatgaa ttag 1094

<210> SEQ ID NO 34
<211> LENGTH: 1063
<212> TYPE: DNA
<213> ORGANISM: Citrobacter youngae

<400> SEQUENCE: 34
atggatagcc cgattccgca gagcggtagc cgtagcgcaa ccctgaccga aggttttaaa 60
gatagcctgc cgattgtgat tagctatatt ccggttgcat ttgcctttgg tctgaatgca 120
acccgtctgg gttttacacc ggttgaaagc gtttttctga gctgtattat ctatgccggt 180
gcaagccagt ttgttattac caccatgctg gcagcaggta gcagcctgtg ggttgcagca 240
ctgaccgtta tggcaatgga tgttcgtcat gttctgtatg gtccgagcct gcgtagccgt 300
attgcacagc gtctgagcaa accgaaaagc gcactgtggg catttggcct gaccgatgaa 360
gtttttgcag cagcaaccgc aaaactggtt cgtgataatc gtcgttggag cgaaaattgg 420
atgattggta ttgcactgtg tagctgggca agctgggttt ttggcaccgc aattggtgca 480
tttagcggta gcggtctgct gaaagattat ccggcagttg aagcagcact gggctttatg 540

-continued

```
ctgcctgcac tgtttatgag ctttctgctg gcgagctttc agcgtaaaca ggcactgtgt    600

gttaccgttg ccctgaccgg tgcactggca ggcgttattc tgtttagcat tccggcagca    660

attctgctgg gtattgtttg tggttgtctg accgcactgc tgcagagctt ttggcagggt    720

ggtccggatg agctatgagg ttctgctgct gggtctgctg gttggttgtg tgaattattg    780

ttttcgttat ctgccgctgc gtctgggtgc aggtaatgtt cgtccggcac gtcgtggtgc    840

aaccggtatc ctgctggata caattggcat tgcaagcatt tgtgcactgc tggtagttag    900

caccgcaccg gaagttatgc atgatgcacg tcgttttgtt ccgaccctgg tgggttttgt    960

tattctgggt gccagcttct ataaaacccg tagcattatt atcccgaccc tgctgagcgc   1020

actgggttat ggtctggcat ggaaaatgct ggtaggtctg taa                     1063
```

```
<210> SEQ ID NO 35
<211> LENGTH: 1063
<212> TYPE: DNA
<213> ORGANISM: Citrobacter freundii

<400> SEQUENCE: 35

atggaaagtc cggttccgca gagcgaaagc agcagcgcaa ccctgaccga aggttttaaa     60

gatagcctgc cgattgtgat tagctatatt ccggttgcat ttgcctttgg tctgaatgca    120

acccgtctgg gttttacacc ggttgaaagc gtgtttttta gctgcattat ctatgccggt    180

gcaagccagt ttgttattac caccatgctg gcagcaggta gcagcctgtg ggttgcagca    240

ctgaccgtta tggcaatgga tgttcgtcat gttctgtatg gtccgagcct gcgtagccgt    300

attgcacagc gtctgagcaa accgaaaagc gcactgtggg catttggcct gaccgatgaa    360

gtttttgcag cagcaaccgc aaaactggtt cgtgataatc gtcgttggag cgaaaattgg    420

atgattggta ttgcactgtg tagctgggca agctgggttt ttggcaccgt tctgggtgca    480

tttagcggta gcggtctgct gaaagattat ccggcagttg aagcagcact gggctttatg    540

ctgcctgcac tgtttatgag ctttctgctg gcgagctttc agcgtaaaca ggcactgtgt    600

gttaccgcag ccctggcagg cgcactggct ggtgttatgc tgtttagcat tccggcagca    660

attctggcag gtattgtttg tggttgtctg accgcactga ttcagagctt ttggcagggt    720

ggtccggatg agctatgaag ttctgctgct gggtctgctg gttggttgtg tgaattattg    780

ttttcgttat ctgccgctgc gtctgggtgt tggtaatgtt cgtccgacca aacgtggtgc    840

aaccggtatt ctgctggata ccattggtat taccagcatt tgtgcactgc tggtagttag    900

caccgcaccg gaagttatgc atgatgcacg tcgttttgtt ccgaccctgg tgggttttgt    960

tatcctgggt gccagcttct ataaaacccg tagcattatt atcccgaccc tgctgagcgc   1020

actgggttat ggtctggcat ggaaaatgct ggttgttctg taa                     1063
```

MICROORGANISM FOR METHIONINE PRODUCTION WITH IMPROVED METHIONINE SYNTHASE ACTIVITY AND METHIONINE EFFLUX

FIELD OF THE INVENTION

The present invention relates to a recombinant microorganism useful for the production of L-methionine and/or its derivatives and process for the preparation of L-methionine. The microorganism of the invention is modified in a way that the L-methionine production is improved by enhancing its cobalamin-dependant methionine synthase activity as well as its L-methionine export. In particular, the genes metH, fldA, fpr or their homologous genes and the genes ygaZ and ygaH or their homologous genes are overexpressed in the microorganism.

PRIOR ART

Sulphur-containing compounds such as cysteine, homocysteine, methionine or S-adenosylmethionine are critical to cellular metabolism. In particular L-methionine, an essential amino acid, which cannot be synthesized by animals, plays an important role in many body functions. Most of the methionine produced industrially is widely used as an animal feed and food additive.

With the decreased use of animal-derived proteins as a result of BSE and chicken flu, the demand for pure methionine has increased. Commonly, D,L-methionine is produced chemically from acrolein, methyl mercaptan and hydrogen cyanide. However, the racemic mixture does not perform as well as pure L-methionine (Saunderson, 1985). Additionally, although pure L-methionine can be produced from racemic methionine, for example, through the acylase treatment of N-acetyl-D,L-methionine, this dramatically increases production costs. Accordingly, the increasing demand for pure L-methionine coupled with environmental concerns render microbial production of methionine an attractive prospect. Other important amino acids, such as lysine, threonine and tryptophan are produced via fermentation for use in animal feed. Therefore, these amino acids can be made using glucose and other renewable resources as starting materials. The production of L-methionine via fermentation has not been successful yet, but the development of the technology is on going.

Different approaches for the optimisation of L-methionine production in microorganisms have been described previously (see, for example, patents or patent applications U.S. Pat. No. 7,790,424, U.S. Pat. No. 7,611,873, WO2002/10209, WO2005/059093 and WO2006/008097); however, industrial production of L-methionine from microorganisms requires further improvements.

In *Escherichia coli*, two distinct enzymes catalyze the terminal step in de novo biosynthesis of methionine; the cobalamin-dependent methionine synthase (MetH, EC 2.1.1.13) which contains a prosthetic group that is required for activity and the cobalamin-independent methionine synthase (MetE, EC 2.1.1.14) (Foster et al., 1961; Gonzalez et al., 1992). The cobalamin-dependent methionine synthase, MetH, is a protein of ~136 kDa containing four domains: a domain containing the cobalamin cofactor (Cob domain), a domain binding the methyl-THF substrate (CH3-THF domain), a domain binding the homocysteine substrate (Hcy domain), and a domain binding S-Adenosyl-Methionine (SAM) (Adomet domain) (Matthews, 2001). In the presence of oxygen, the enzyme is inactivated by oxidation (Banerjee et al., 1990). In order to reactivate the enzyme, a reductive methylation occurs. The reaction involves a methyl group provided by SAM bound to the AdoMet domain of the enzyme, and two electrons transferred via an external transport chain. The two electrons are provided by NADPH and transferred via a downhill potential driven redox chain composed of a FAD-containing flavodoxine reductase, FldA and a FMN-containing flavodoxine reductase, Fpr (Fujii & Huennekens, 1974; Wan & Jarrett, 2002) in *Escherichia coli*. As disclosed in patent application WO2009/144270, in *Corynebacterium glutamicum*, functional homologues of FldA and Fpr have been identified. They are respectively FdxC, FdxD or FdxA and FprA1, FprA2, FprA3 or FldR1.

The protein complex YgaZ and YgaH is a member of the branched chain amino acid exporter (LIV-E) family responsible for export of L-valine. In the same manner, YgaZH is also involved in the export of methionine as it was shown by Trotschel and colleagues for BrnFE, the homolog of YgaZH from *Corynebacterium glutamicum* (Trotschel et al., 2005).

Numerous patents applications were filed on the improvement of the methionine synthase activity by different means in order to produce L-methionine:

- WO2007/012078 and WO2007/135188 from BASF claim among other modifications, genetic alteration leading to overexpression of at least metH and/or metE,
- WO2009/144270 from Evonik discloses a method of producing methionine with a microorganism that displays an increased amount and/or activity of a cob(I)alamin-dependent MetH reactivation system,
- WO2008/080900 from Evonik claims a $MetH^{FBR}$ form (FeedBack Resistant) which should be more resistant to high L-methionine concentrations.

In the same manner few patents disclose the overexpression of genes encoding the methionine excretion system in different micro organisms:

- Reduction of the L-methionine uptake in *Corynebacterium* is described in patent applications WO2002/097096 and WO2005/085463 (Degussa) or,
- Overexpression of a branched chain amino acid exporter (YgaZH) responsible for the export of L-valine and L-methionine is disclosed in patent applications EP1239041 (Ajinomoto) and WO2008/082211 (CJ Corporation).

Inventors have found surprisingly and unexpectedly that the increase of the L-methionine efflux together with the enhancement of the cobalamin-dependant L-methionine synthase activity in a recombinant L-methionine overproducer microorganism improve the methionine production.

SUMMARY OF THE INVENTION

The invention relates to recombinant microorganism and method for optimising the production of methionine and/or its derivatives, wherein the cobalamin-dependent methionine synthase activity and the methionine efflux are enhanced. In the recombinant microorganism, cobalamin-dependent methionine synthase activity is enhanced by overexpressing the expression of metH, and optionally the expression of the genes fldA and fpr from *E. coli* or their homologous genes from *C. glutamicum* whereas methionine efflux is enhanced by overexpressing the genes ygaZH from *E. coli* or brnFE from *C. glutamicum* or their homologous genes.

The recombinant microorganism may also comprise other genetic modifications such as:

- an increased expression of at least one of the following genes: ptsG, pyc, pntAB, cysP, cys U, cys W, cysA, cysM, cysJ, cysI, cysH, gcvT, gcvH, gcvP, lpd, serA, serB, serC, cysE, metF, metA, metA* allele encoding for an enzyme with reduced feed-back sensitivity to S-adenosylmethionine and/or methionine, thrA, or a thrA* allele encoding for an enzyme with reduced feed-back inhibition to threonine and/or an attenuated expression of one of the following genes: metJ, pykA, pykF, purU, ybdL, udhA, dgsA, metE, metN, metI, metQ or yncA.

In a particular embodiment, the present invention is related to a recombinant microorganism wherein: a) the genes metH, and optionally the genes fldA and fpr from *E. coli* or their homologous genes from *C. glutamicum* are overexpressed, b) the genes ygaZ and ygaH from *E. coli* or the genes brnF and brnE from *C. glutamicum* or their homologous genes originating from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii* are overexpressed, and c) the expression of the genes metA*, cysPUWAM, cysJIH, gcvTHP, metF, serA, serB, serC, cysE, thrA*, ptsG and pyc are enhanced; and d) the expression of the genes metJ, pykA, pykF, purU, yncA, dgsA and metE are attenuated.

Preferably, the recombinant microorganism is *Escherichia coli* or *Corynebacterium glutamicum.*

DETAILED DESCRIPTION OF THE INVENTION

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting, which will be limited only by the appended claims.

All publications, patents and patent applications cited herein, whether supra or infra, are hereby incorporated by reference in their entirety.

Furthermore, the practice of the present invention employs, unless otherwise indicated, conventional microbiological and molecular biological techniques within the skill of the art. Such techniques are well known to the skilled worker, and are explained fully in the literature.

It must be noted that as used herein and in the appended claims, the singular forms "a", "an", and "the" include plural reference unless the context clearly dictates otherwise. Thus, for example, a reference to "a microorganism" includes a plurality of such microorganisms, and a reference to "an endogenous gene" is a reference to one or more endogenous genes, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

In the claims that follow and in the consecutive description of the invention, except where the context requires otherwise due to express language or necessary implication, the word "comprise", "contain", "involve" or "include" or variations such as "comprises", "comprising", "containing", "involved", "includes", "including" are used in an inclusive sense, i.e. to specify the presence of the stated features but not to preclude the presence or addition of further features in various embodiments of the invention.

The term "methionine" and "L-methionine" designate the essential sulphur-containing amino-acid with chemical formula $HO_2CCH(NH_2)CH_2CH_2SCH_3$ and CAS number 59-51-8 or 63-68-3 for the specific L-isomer.

"Derivatives of methionine" refers to molecules analogs to methionine which present the same chemical backbone but differ from methionine with at least one chemical group. In this invention, preferred methionine derivatives are N-acetyl methionine (NAM), S-adenosyl methionine (SAM) and hydroxy-methionine (or methionine hydroxy analogue or MHA).

The term "microorganism", as used herein, refers to a bacterium, yeast or fungus which is not modified artificially. Preferentially, the microorganism is selected among Enterobacteriaceae, Bacillaceae, Streptomycetaceae and Corynebacteriaceae. More preferentially the microorganism is a species of *Escherichia, Klebsiella, Pantoea, Salmonella*, or *Corynebacterium*. Even more preferentially the microorganism of the invention is either the species *Escherichia coli* or *Corynebacterium glutamicum.*

The term "recombinant microorganism" or "genetically modified microorganism", as used herein, refers to a bacterium, yeast or fungus that is not found in nature and is genetically different from its equivalent found in nature. It means, it is modified either by introduction or by deletion or by modification of genetic elements. It can also be transformed by forcing the development and evolution of new metabolic pathways by combining directed mutagenesis and evolution under specific selection pressure (see, for example, WO2004/076659 or WO2007/011939).

A microorganism may be modified to express exogenous genes if these genes are introduced into the microorganism with all the elements allowing their expression in the host microorganism. The modification or "transformation" of microorganisms with exogenous DNA is a routine task for those skilled in the art.

A microorganism may be modified to modulate the expression level of an endogenous gene.

The term "endogenous gene" means that the gene was present in the microorganism before any genetic modification. Endogenous genes may be overexpressed by introducing heterologous sequences in addition to, or to replace endogenous regulatory elements, or by introducing one or more supplementary copies of the gene into the chromosome or a plasmid. Endogenous genes may also be modified to modulate their expression and/or activity. For example, mutations may be introduced into the coding sequence to modify the gene product or heterologous sequences may be introduced in addition to or to replace endogenous regulatory elements. Modulation of an endogenous gene may result in the up-regulation and/or enhancement of the activity of the gene product, or alternatively, down regulate and/or lower the activity of the endogenous gene product.

Another way to modulate their expression is to exchange the endogenous promoter of a gene (e.g., wild type promoter) with a stronger or weaker promoter to up or down regulate expression of the endogenous gene. These promoters may be homologous or heterologous. It is well within the ability of the person skilled in the art to select appropriate promoters.

Contrariwise, "exogenous gene" means that the gene was introduced into a microorganism, by means well known by the man skilled in the art whereas this gene is not naturally occurring in the microorganism. Exogenous genes may be integrated into the host chromosome, or be expressed extrachromosomally by plasmids or vectors. A variety of plasmids, which differ with respect to their origin of replication and their copy number in the cell, are well known in the art. These genes may be homologous.

In the context of the invention, the term "homologous gene" is not limited to designate genes having a theoretical common genetic ancestor, but includes genes which may be genetically unrelated that have, none the less, evolved to encode protein which perform similar functions and/or have similar structure. Therefore the term 'functional homolog" for the purpose of the present invention relates to the fact that a certain enzymatic activity may not only be provided by a specific protein of defined amino acid sequence, but also by proteins of similar sequence from other (un)related microorganisms.

Using the references given in Genbank for known genes, those skilled in the art are able to determine the equivalent genes in other organisms, bacterial strains, yeast, fungi, mammals, plants, etc. This routine work is advantageously done using consensus sequences that can be determined by carrying out sequence alignments with genes derived from other microorganisms and designing degenerate probes to clone the corresponding gene in another organism. These routine methods of molecular biology are well known to those skilled in the art.

The terms "improved methionine production", "improve methionine production" and grammatical equivalents thereof, as used herein, refer to an increased methionine/carbon source yield (ratio of gram/mol methionine produced per gram/mol carbon source consumed that it can be expressed in percent) and/or an improved purity of produced methionine. In this invention, the purity of the produced methionine may be increased by decreasing the production of ketomethylvalerate and/or homolanthionine. Methods for determining the amount of carbon source consumed and of methionine produced are well known to those in the art. The yield and/or the purity of produced methionine are higher in the recombinant microorganism compared to the corresponding unmodified microorganism.

The terms "microorganism optimised for the fermentative production of methionine" refers to microorganisms evolved and/or genetically modified to present an improved methionine production in comparison with the endogenous production of the corresponding wild-type microorganisms. Such microorganisms "optimised" for methionine production are well known in the art, and have been disclosed in particular in patent applications WO2005/111202, WO2007/077041, WO2009/043803 and WO2012/098042.

According to the invention the terms "fermentative production", "culture" or "fermentation" are used to denote the growth of bacteria. This growth is generally conducted in fermenters with an appropriate culture medium adapted to the microorganism being used and containing at least one simple carbon source, and if necessary co-substrates.

An "appropriate culture medium" designates a medium (e.g., a sterile, liquid media) comprising nutrients essential or beneficial to the maintenance and/or growth of the cell such as carbon sources or carbon substrates, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids and vitamins.

The term "carbon source" or "carbon substrate" or "source of carbon" according to the present invention denotes any source of carbon that can be used by those skilled in the art to support the normal growth of a microorganism, including monosaccharides (such as glucose, galactose, xylose, fructose or lactose), oligosaccharides, disaccharides (such as sucrose, cellobiose or maltose), molasses, starch or its derivatives, hemicelluloses and combinations thereof. An especially preferred simple carbon source is glucose. Another preferred simple carbon source is sucrose. The carbon source can be derived from renewable feed-stock. Renewable feed-stock is defined as raw material required for certain industrial processes that can be regenerated within a brief delay and in sufficient amount to permit its transformation into the desired product. Vegetal biomass treated or not, is an interesting renewable carbon source.

The term "source of sulphur" according to the invention refers to sulphate, thiosulfate, hydrogen sulphide, dithionate, dithionite, sulphite, methylmercaptan, dimethylsulfide and other methyl capped sulphides or a combination of the different sources. More preferentially, the sulphur source in the culture medium is sulphate or thiosulfate or a mixture thereof.

The terms "source of nitrogen" corresponds to either an ammonium salt or ammoniac gas. The nitrogen source is supplied in the form of ammonium or ammoniac.

The terms "attenuation" or "expression attenuated" mean in this context that the expression of a gene or the production of an enzyme is decreased or suppressed compared to the non modified microorganism leading to a decrease in the intracellular concentration of a ribonucleic acid, a protein or an enzyme compared to the non modified microorganism. The man skilled in the art knows different means and methods to measure ribonucleic acid concentration or protein concentration in the cell including for instance use of Reverse Transcription Polymerase Chain Reaction (RT-PCR) and Real-time Polymerase Chain Reaction (qPCR) to determine ribonucleic acid concentration and use of specific antibody to determine concentration of specific protein.

Decrease or suppression of the production of an enzyme is obtained by the attenuation of the expression of gene encoding said enzyme.

Attenuation of genes may be achieved by means and methods known to the man skilled in the art. Generally, attenuation of gene expression may be achieved by:

- Mutating the coding region or the promoter region or,
- Deleting of all or a part of the promoter region necessary for the gene expression or,
- Deleting of all or a part of the coding region of the gene by homologous recombination or,
- Inserting an external element into coding region or into promoter region or,
- Expressing the gene under control of a weak promoter or an inducible promoter.

The man skilled in the art knows a variety of promoters which exhibit different strength and which promoter to use for a weak or an inducible genetic expression.

The term "activity" of an enzyme is used interchangeably with the term "function" and designates, in the context of the invention, the reaction that is catalyzed by the enzyme. The man skilled in the art knows how to measure the enzymatic activity of said enzyme.

The terms "attenuated activity" or "reduced activity" of an enzyme mean either a reduced specific catalytic activity of the protein obtained by mutation in the aminoacids sequence and/or decreased concentrations of the protein in the cell obtained by mutation of the nucleotidic sequence or by deletion of the coding region of the gene.

The terms "enhanced activity" or "increased activity" of an enzyme designate either an increased specific catalytic activity of the enzyme, and/or an increased quantity/availability of the enzyme in the cell, obtained for example by overexpressing the gene encoding the enzyme.

The terms “increased expression”, “enhanced expression” or “overexpression” and grammatical equivalents thereof, are used interchangeably in the text and have a similar meaning. These terms mean that the expression of a gene or the production of an enzyme is increased compared to the non modified microorganism leading to an increase in the intracellular concentration of a ribonucleic acid, a protein or an enzyme compared to the non modified microorganism. The man skilled in the art knows different means and methods to measure ribonucleic acid concentration or protein concentration in the cell including for instance use of Reverse Transcription Polymerase Chain Reaction (RT-PCR) and Real-time Polymerase Chain Reaction (qPCR) to determine ribonucleic acid concentration and use of specific antibody to determine concentration of specific protein.

Increase production of an enzyme is obtained by increasing expression of the gene encoding said enzyme.

To increase the expression of a gene, the man skilled in the art knows different techniques such as:

- Increasing the number of copies of the gene in the microorganism. The gene is encoded chromosomally or extrachromosomally. When the gene is located on the chromosome, several copies of the gene can be introduced on the chromosome by methods of recombination, known by the expert in the field (including gene replacement). When the gene is located extra-chromosomally, it may be carried by different types of plasmids that differ with respect to their origin of replication and thus their copy number in the cell. These plasmids are present in the microorganism in 1 to 5 copies, or about 20 copies, or up to 500 copies, depending on the nature of the plasmid: low copy number plasmids with tight replication (e.g for *E. coli* pSC101, RK2), low copy number plasmids (e.g for *E. coli* pACYC, pRSF1010) or high copy number plasmids (e.g for *E. coli* pSK bluescript II).
- Using a promoter leading to a high level of expression of the gene. The man skilled in the art knows which promoters are the most convenient, for example promoters Ptrc, Ptac, Plac, or the lambda promoter a are widely used. These promoters can be “inducible” by a particular compound or by specific external condition like temperature or light. These promoters may be homologous or heterologous.
- Attenuating the activity or the expression of a transcription repressor, specific or non-specific of the gene.
- Using elements stabilizing the corresponding messenger RNA (Carrier and Keasling, 1999) or elements stabilizing the protein (e.g., GST tags, GE Healthcare).

The terms “encoding” or “coding” refer to the process by which a polynucleotide, through the mechanisms of transcription and translation, produces an amino-acid sequence. The gene(s) encoding the enzyme(s) can be exogenous or endogenous.

The terms “feed-back sensitivity” or “feed-back inhibition” refer to a cellular mechanism control in which an or several enzymes that catalyse the production of a particular substance in the cell are inhibited or less active when that substance has accumulated to a certain level. So the terms “reduced feed-back sensitivity” or “reduced feed-back inhibition” mean that the activity of such a mechanism is decreased or suppressed compared to a non modified microorganism. The man skilled in the art knows how to modify the enzyme to obtain this result. Such modifications have been described in the patent application WO2005/111202 or in the U.S. Pat. No. 7,611,873.

In a first aspect of the invention, a recombinant microorganism is optimised for the fermentative production of methionine and/or its derivatives by enhancing the cobalamin-dependent methionine synthase activity and by enhancing the methionine efflux in said microorganism. Preferably, the recombinant microorganism is chosen among Enterobacteriaceae or Corynebacteriaceae. More preferably, the recombinant microorganism of the invention is chosen among *Escherichia coli* or *Corynebacterium glutamicum.*

As described above, cobalamin-dependent methionine synthase activity is mediated by MetH enzyme. This enzyme needs a reactivation system for having a sustained activity. This system is encoded by two genes, fldA and fpr in *E. coli* and by respectively gene chosen among fdxC, fdxD or fdxA and among fprA1, fprA2, fprA3 or fldR1 in *C. glutamicum*. In this application, the terms “MetH and its reactivation system” or “metH, fldA, fpr” relate to the cobalamin-dependent methionine synthase and its reactivation system both in *E. coli* and in *C. glutamicum* or their encoding genes both from *E. coli* and from *C. glutamicum*. Thus, enhancement of cobalamin-dependent methionine synthase activity is preferably carried out by overexpression of metH gene and also of its reactivation system encoded by fldA and fpr genes.

In one embodiment of the invention, the cobalamin-dependent methionine synthase activity is enhanced by overexpressing (enhancing their expression) genes metH, fldA, fpr from *E. coli* or their homologous genes from *C. glutamicum*. Preferably, these genes are overexpressed under a promoter different from their wild-type promoter.

More preferably, the genes metH, fldA or fpr or their homologous genes from *C. glutamicum* are overexpressed chromosomally, i.e. these genes are overexpressed from the chromosome. One or several supplementary copies of each gene are introduced on the chromosome of the microorganism. They are integrated at different loci selected from the list disclosed in the patent application WO2011/073122, and whose deletions do not have impact on methionine production. The wild-type copy of the coding sequence of each gene is conserved, but their promoter region may be replaced by artificial promoter and/or Ribosome Binding Site (RBS).

In a specific embodiment of the invention:

- wild-type metH gene is conserved with replacement of its natural promoter and RBS, and two additional copies are introduced on the chromosome, and
- wild-type fldA and fpr genes and their promoter regions are conserved, and one additional copy of each gene is introduced on the chromosome.

Additional copies of the introduced genes are expressed under control of artificial promoter and RBS.

In amino-acid producer microorganisms, methionine is excreted by a specific efflux transporter. Notably, in *E. coli*, this transporter is called YgaZH and is encoded by the ygaZ and ygaH genes whereas in *C. glutamicum*, it is named BrnFE and is encoded by the brnF and brnE genes. Functional homologues of this methionine efflux system have been identified in several other microorganisms. In the invention, recombinant microorganism overexpresses ygaZH genes from *E. coli* or brnFE genes from *C. glutamicum*. Alternatively, the recombinant microorganism of the invention may overexpress functional homologues of YgaZH or of BrnFE transporters. YgaZ and YgaH homologous protein are presented respectively in Table 1 and Table 2.

TABLE 1

| YgaZ homologous proteins | | |
|---|---|---|
| Acession Number | Name | Organism |
| YP_001455539.1 NC_009792.1. ABV15103.1 | hypothetical protein CKO_04031 [*Citrobacter koseri* ATCC BAA-895] | *Citrobacter koseri* |
| WP_005122932.1 EIQ78635.1 | membrane protein [*Shigella flexneri*] | *Shigella flexneri* |
| YP_007877063.1 AGJ89511.1 WP_015585890.1 | hypothetical protein RORB6_24155 [*Raoultella ornithinolytica* B6] | *Raoultella ornithinolytica* |
| YP_008107733.1 AGN85393.1 WP_020454909.1 | membrane protein [*Enterobacter* sp. R4-368] | *Enterobacter* sp. |
| WP_004959353.1 EFE95945.1 | membrane protein [*Serratia odorifera*] | *Serratia odorifera* |
| YP_003884334.1 ADM99777.1 | amino acid transporter [*Dickeya dadantii* 3937] *Erwinia chrysanthemi* (strain 3937) | *Dickeya dadantii* |
| YP_006647984.1 AFR04731.1 | amino acid transporter [*Pectobacterium carotovorum* subsp. *carotovorum* PCC21] | *Pectobacterium carotovorum* subsp. *Carotovorum* |
| YP_001007412.1 CAL13268.1 | putative amino acid transporter [*Yersinia enterocolitica* subsp. *enterocolitica* 8081] | *Yersinia enterocolitica* subsp. *Enterocolitica* |
| NP_928590.1 CAE13573.1 | hypothetical protein plu1279 [*Photorhabdus luminescens* subsp. *laumondii* TTO1] | *Photorhabdus luminescens* subsp. *Laumondii* |
| WP_004847360.1 EHM42581.1 | membrane protein [*Hafnia alvei*] | *Hafnia alvei* |
| WP_016157304.1 EOQ28426.1 | inner membrane protein YgaZ [*Citrobacter* sp. KTE32] | *Citrobacter* sp. KTE32 |
| WP_006687199.1 EFE06904.1 | membrane protein [*Citrobacter youngae*] putative azaleucine resistance protein AzlC [*Citrobacter youngae* ATCC 29220] | *Citrobacter youngae* |
| YP_005198838.1 AEX50698.1 | putative branched-chain amino acid permease (azaleucine resistance) [*Rahnella aquatilis* CIP 78.65 = ATCC 33071] | *Rahnella aquatilis* |
| WP_009111644.1 EHD20336.1. | membrane protein [*Brenneria* sp. EniD312] | *Brenneria* sp. |
| YP_003469114.1 CBJ82350.1 | amino acid transporter [*Xenorhabdus bovienii* SS-2004] | *Xenorhabdus bovienii* |
| WP_000841919.1 | membrane protein [*Shigella flexneri*] | *Shigella flexneri* |
| WP_000445647.1 | membrane protein [*Shigella dysenteriae*] | *Shigella dysenteriae* |
| WP_000445645.1 | membrane protein [*Shigella flexneri*] | *Shigella flexneri* |
| EFP71467.1 | azlC family protein [*Shigella dysenteriae* 1617] | *Shigella dysenteriae* |
| WP_005063865.1 | membrane protein [*Shigella flexneri*] | *Shigella flexneri* |
| WP_001428008.1 | membrane protein [*Shigella dysenteriae*] | *Shigella dysenteriae* |
| WP_005031133.1 | membrane protein [*Shigella dysenteriae*] | *Shigella dysenteriae* |
| WP_004993748.1 | membrane protein [*Shigella boydii*] | *Shigella boydii* |
| WP_005099151.1 | membrane protein [*Shigella flexneri*] | *Shigella flexneri* |
| NP_708495.1 | hypothetical protein SF2709 [*Shigella flexneri* 2a str. 301] | *Shigella flexneri* |
| YP_409184.1. NC_007613.1. ABB67356 | hypothetical protein SBO_2835 [*Shigella boydii* Sb227] | *Shigella boydii* |
| WP_005119769.1 | branched-chain amino acid permease [*Shigella flexneri*] | *Shigella flexneri* |
| WP_003825971.1 | membrane protein [*Citrobacter* sp. 30_2] | *Citrobacter* sp. |
| WP_016154156.1 | inner membrane protein YgaZ [*Citrobacter* sp. KTE151] | *Citrobacter* sp. |
| WP_003839672.1 | hypothetical protein [*Citrobacter freundii*] | *Citrobacter freundii* |
| WP_016150871.1 | inner membrane protein YgaZ [*Citrobacter* sp. KTE30] | *Citrobacter* sp. |
| WP_019077531.1 | membrane protein [*Citrobacter freundii*] | *Citrobacter freundii* |
| WP_003037292.1 | membrane protein [*Citrobacter* sp. L17] | *Citrobacter* sp. |
| WP_009652545.1 | membrane protein [*Klebsiella* sp. OBRC7] | *Klebsiella* sp. |
| WP_004853460.1 | membrane protein [*Klebsiella oxytoca*] | *Klebsiella oxytoca* |
| YP_005016079.1 | AzlC family protein [*Klebsiella oxytoca* KCTC 1686] | *Klebsiella oxytoca* |
| WP_004866792.1 | membrane protein [*Klebsiella oxytoca*] | *Klebsiella oxytoca* |
| WP_017459327.1 | membrane protein [*Enterobacter cloacae*] | *Enterobacter cloacae* |
| WP_004205700.1 | AzlC family protein [*Klebsiella pneumoniae*] | *Klebsiella pneumoniae* |
| CDA02044.1 | azlC family protein [*Klebsiella variicola* CAG:634] | *Klebsiella variicola* |
| WP_004123979.1 | membrane protein [*Klebsiella oxytoca*] | *Klebsiella oxytoca* |
| WP_004132932.1 | azlC family protein [*Klebsiella oxytoca*] | *Klebsiella oxytoca* |
| WP_017900616.1 | membrane protein [*Klebsiella pneumoniae*] | *Klebsiella pneumoniae* |
| YP_002236980.1 | AzlC family protein [*Klebsiella pneumoniae* 342] | *Klebsiella pneumoniae* |
| YP_005228384.1 | putative amino acid transport protein [*Klebsiella pneumoniae* subsp. *pneumoniae* HS11286] | *Klebsiella pneumoniae* subsp. *Pneumoniae* |

TABLE 1-continued

| YgaZ homologous proteins | | |
|---|---|---|
| Acession Number | Name | Organism |
| YP_001336647.1 | putative amino acid transport protein [*Klebsiella pneumoniae* subsp. *pneumoniae* MGH 78578] | *Klebsiella pneumoniae* subsp. *Pneumoniae* |
| WP_016947585.1 | membrane protein [*Klebsiella pneumoniae*] | *Klebsiella pneumoniae* |
| YP_005956056.1 | putative amino acid transport protein [*Klebsiella pneumoniae* KCTC 2242] | *Klebsiella pneumoniae* |
| WP_020803754.1 | inner membrane protein YgaZ [*Klebsiella pneumoniae*] | *Klebsiella pneumoniae* |
| WP_016161678.1 | inner membrane protein YgaZ [*Klebsiella* sp. KTE92] | *Klebsiella* sp. |
| WP_004174723.1 | membrane protein [*Klebsiella pneumoniae*] | *Klebsiella pneumoniae* |
| WP_004114705.1 | membrane protein [*Klebsiella oxytoca*] | *Klebsiella oxytoca* |
| YP_007990259.1 | ygaZ [*Klebsiella pneumoniae*] | *Klebsiella pneumoniae* |
| WP_004104780.1 | membrane protein [*Klebsiella oxytoca*] | *Klebsiella oxytoca* |
| WP_007370573.1 | membrane protein [*Kosakonia radicincitans*] | *Kosakonia radicincitans* |
| WP_007370573.1 | membrane protein [*Kosakonia radicincitans*] | *Kosakonia radicincitans* |
| NP_668256.1 | hypothetical protein y0925 [*Yersinia pestis* KIM10+] | *Yersinia pestis* |
| WP_005119769.1 | branched-chain amino acid permease [*Shigella flexneri*] | *Shigella flexneri* |
| YP_069400.1 | LIV-E family branched chain amino acid exporter large subunit [*Yersinia pseudotuberculosis* IP 32953] | *Yersinia pseudotuberculosis* |
| WP_017893772.1 | membrane protein [*Serratia* sp. S4] | *Serratia* sp. |
| YP_001479963.1 | AzlC family protein [*Serratia proteamaculans* 568] | *Serratia proteamaculans* |
| WP_005189088.1 | membrane protein [*Yersinia intermedia*] | *Yersinia intermedia* |
| YP_004297214.1 | putative amino acid transporter [*Yersinia enterocolitica* subsp. *palearctica* 105.5R(r)] | *Yersinia enterocolitica* subsp. *Palearctica* |
| WP_019081387.1 | membrane protein [*Yersinia enterocolitica*] | *Yersinia enterocolitica* |
| WP_004392936.1 | membrane protein [*Yersinia kristensenii*] | *Yersinia kristensenii* |
| WP_016929851.1 | membrane protein [*Serratia marcescens*] | *Serratia marcescens* |
| WP_019845222.1 | membrane protein [*Dickeya zeae*] | *Dickeya zeae* |
| YP_003334823.1 | AzlC family protein [*Dickeya dadantii* Ech586] | *Dickeya dadantii* |
| YP_003042011.1 | conserved hypothetical protein [*Photorhabdus asymbiotica*] | *Photorhabdus asymbiotica* |
| WP_016941678.1 | membrane protein [*Dickeya zeae*] | *Dickeya zeae* |
| WP_005274999.1 | membrane protein [*Yersinia bercovieri*] | *Yersinia bercovieri* |
| CAC44347.1 | YgaZ protein [*Erwinia chrysanthemi*] | *Erwinia chrysanthemi* |
| WP_004704053.1 | membrane protein [*Yersinia aldovae*] | *Yersinia aldovae* |
| YP_003003219.1 | AzlC family protein [*Dickeya zeae* Ech1591] | *Dickeya zeae* |
| WP_004707388.1 | membrane protein [*Yersinia frederiksenii*] | *Yersinia frederiksenii* |
| WP_008812528.1 | membrane protein [*Enterobacteriaceae bacterium* 9_2_54FAA] | *Enterobacteriaceae bacterium* |
| YP_008231812.1 | membrane protein [*Serratia liquefaciens* ATCC 27592] | *Serratia liquefaciens* |
| YP_051597.1 | amino acid transporter [*Pectobacterium atrosepticum* SCRI1043] | *Pectobacterium atrosepticum* |
| WP_019455591.1 | membrane protein [*Serratia marcescens*] | *Serratia marcescens* |
| YP_007407667.1 AGE19648.1 NC_020211.1. | putative amino acid transporter YgaZ [*Serratia marcescens* WW4] | *Serratia marcescens* |
| WP_004716726.1 | membrane protein [*Yersinia rohdei*] | *Yersinia rohdei* |
| YP_003018879.1 | AzlC family protein [*Pectobacterium carotovorum* subsp. *carotovorum* PC1] | *Pectobacterium carotovorum* subsp. *Carotovorum* |
| WP_004873538.1 | membrane protein [*Yersinia mollaretii*] | *Yersinia mollaretii* |
| WP_005975645.1 | membrane protein [*Pectobacterium wasabiae*] | *Pectobacterium wasabiae* |
| YP_003260827.1 | AzlC family protein [*Pectobacterium wasabiae* WPP163] | *Pectobacterium wasabiae* |
| YP_002986523.1 | AzlC family protein [*Dickeya dadantii* Ech703] | *Dickeya dadantii* |
| YP_007345875.1 AGB83690.1 | putative branched-chain amino acid permease (azaleucine resistance) [*Serratia marcescens* FGI94] | *Serratia marcescens* |
| YP_004211503.1 | AzlC family protein [*Rahnella* sp. Y9602] | *Rahnella* sp. |
| YP_005400523.1 | AzlC family protein [*Rahnella aquatilis* HX2] | *Rahnella aquatilis* |
| WP_010305354.1 | membrane protein [*Pectobacterium carotovorum*] | *Pectobacterium carotovorum* |
| WP_010848732.1 | conserved hypothetical protein [*Xenorhabdus nematophila*] | *Xenorhabdus nematophila* |
| YP_003711585.1 CBJ89380.1 | hypothetical protein XNC1_1315 [*Xenorhabdus nematophila* ATCC 19061] | *Xenorhabdus nematophila* |
| YP_006500218.1 AFN33798.1 | hypothetical protein A225_4537 [*Klebsiella oxytoca* E718] | *Klebsiella oxytoca* |
| EHT06520.1 | inner membrane protein YgaZ [*Klebsiella oxytoca* 10-5246] | *Klebsiella oxytoca* |

TABLE 1-continued

YgaZ homologous proteins

| Acession Number | Name | Organism |
|---|---|---|
| EKP29343.1 | AzlC family protein [*Klebsiella oxytoca* M5aI] | *Klebsiella oxytoca* |
| EJK15416.1 | putative amino acid transport protein [*Klebsiella pneumoniae* subsp. *pneumoniae* KPNIH18] | *Klebsiella pneumoniae* subsp. *Pneumoniae* |
| YP_006500218.1 | hypothetical protein A225_4537 [*Klebsiella oxytoca* E718] | *Klebsiella oxytoca* |
| YP_002920871.1 | putative amino acid transport protein [*Klebsiella pneumoniae* subsp. *pneumoniae* NTUH-K2044] | *Klebsiella pneumoniae* subsp. *Pneumoniae* |
| YP_003437997.1 | AzlC family protein [*Klebsiella variicola* At-22] | *Klebsiella variicola* |
| YP_003260827.1 | AzlC family protein [*Pectobacterium wasabiae* WPP163] | *Pectobacterium wasabiae* |
| WP_010305354.1 | membrane protein [*Pectobacterium carotovorum*] | *Pectobacterium carotovorum* |
| YP_404404.1 ABB62913.1 | hypothetical protein SDY_2877 [*Shigella dysenteriae* Sd197] | *Shigella dysenteriae* |
| YP_311671.1. NC_007384.1. AAZ89436.1 | hypothetical protein SSON_2826 [*Shigella sonnei* Ss046] | *Shigella sonnei* |

TABLE 2

YgaH homologous proteins

| Acession Number | Name | Organism |
|---|---|---|
| YP_001455540.1 ABV15104.1 | hypothetical protein CKO_04032 [*Citrobacter koseri* ATCC BAA-895] | *Citrobacter koseri* |
| WP_005122930.1 EIQ78634.1 | branched-chain amino acid ABC transporter permease [*Shigella flexneri*] | *Shigella flexneri* |
| YP_007877062.1 AGJ89510.1 | L-valine exporter [*Raoultella ornithinolytica* B6] | *Raoultella ornithinolytica* |
| YP_008107734.1 WP_020454910.1 AGN85394.1 | branched-chain amino acid ABC transporter permease [*Enterobacter* sp. R4-368] | *Enterobacter* sp. |
| WP_004959351.1 EFE95944.1 | branched-chain amino acid ABC transporter permease [*Serratia odorifera*] | *Serratia odorifera* |
| YP_003884335.1 ADM99778.1 | hypothetical protein Dda3937_00895 [*Dickeya dadantii* 3937] | *Dickeya dadantii* |
| YP_006647985.1 AFR04732.1 | hypothetical protein PCC21_033290 [*Pectobacterium carotovorum* subsp. *carotovorum* PCC21] | *Pectobacterium carotovorum* subsp. *carotovorum* |
| YP_001007413.1 CAL13269.1 | hypothetical protein YE3239 [*Yersinia enterocolitica* subsp. *enterocolitica* 8081] | *Yersinia enterocolitica* subsp. *enterocolitica* |
| NP_928589.1 CAE13572.1 | hypothetical protein plu1278 [*Photorhabdus luminescens* subsp. *laumondii* TTO1] | *Photorhabdus luminescens* subsp. *laumondii* |
| WP_004847362.1 EHM42582.1 | branched-chain amino acid ABC transporter permease [*Hafnia alvei*] | *Hafnia alvei* |
| WP_016154157.1 EOQ28427.1 EOQ47452.1 | L-valine exporter [*Citrobacter* sp. KTE32] | *Citrobacter* sp. |
| WP_006687198.1 EFE06903.1 | branched-chain amino acid ABC transporter permease [*Citrobacter youngae*] | *Citrobacter youngae* |
| YP_005198837.1 AEX50697.1 | Branched-chain amino acid transport protein AzlD [*Rahnella aquatilis* CIP 78.65 = ATCC 33071] | *Rahnella aquatilis* |
| WP_009111643.1 EHD20335.1. | branched-chain amino acid ABC transporter permease [*Brenneria* sp. EniD312] | *Brenneria* sp. EniD312 |
| YP_003469115.1 CBJ82351.1 | transporter [*Xenorhabdus bovienii* SS-2004] | *Xenorhabdus bovienii* |
| NP_708496.1 | L-valine exporter [*Shigella flexneri* 2a str. 301] | *Shigella flexneri* |
| YP_409183.1. NC_007613.1. ABB67355.1. | conserved hypothetical protein [*Shigella boydii* Sb227] | *Shigella boydii* |
| WP_000119765.1 | branched-chain amino acid ABC transporter permease [*Shigella flexneri*] | *Shigella flexneri* |
| WP_003825969.1 | branched-chain amino acid ABC transporter permease [*Citrobacter* sp. 30_2] | *Citrobacter* sp. |
| WP_003037297.1 | branched-chain amino acid ABC transporter permease [*Citrobacter freundii*] | *Citrobacter freundii* |
| WP_003037297.1 | branched-chain amino acid ABC transporter permease [*Citrobacter freundii*] | *Citrobacter freundii* |

TABLE 2-continued

| YgaH homologous proteins | | |
|---|---|---|
| Acession Number | Name | Organism |
| EKU35015 | liv-e family branched chain amino acid small subunit [*Citrobacter* sp. L17] | *Citrobacter* sp. |
| WP_009652550.1 | branched-chain amino acid ABC transporter permease [*Klebsiella* sp. OBRC7] | *Klebsiella* sp. |
| WP_004853462.1 | branched-chain amino acid ABC transporter permease [*Klebsiella oxytoca*] | *Klebsiella oxytoca* |
| YP_005016080.1 | putative L-valine exporter [*Klebsiella oxytoca* KCTC 1686] | *Klebsiella oxytoca* |
| WP_017459326.1 | branched-chain amino acid ABC transporter permease [*Enterobacter cloacae*] | *Enterobacter cloacae* |
| WP_004205699.1 | L-valine exporter [*Klebsiella pneumoniae*] | *Klebsiella pneumoniae* |
| WP_004123982.1 | branched-chain amino acid ABC transporter permease [*Klebsiella oxytoca*] | *Klebsiella oxytoca* |
| WP_004132928.1 | L-valine exporter [*Klebsiella oxytoca*] | *Klebsiella oxytoca* |
| YP_002236979.1 | hypothetical protein KPK_1115 [*Klebsiella pneumoniae* 342] | *Klebsiella pneumoniae* |
| YP_005228385.1 | hypothetical protein KPHS_40850 [*Klebsiella pneumoniae* subsp. *pneumoniae* HS11286] | *Klebsiella pneumoniae* subsp. *Pneumoniae* |
| YP_001336648.1 | hypothetical protein KPN_03012 [*Klebsiella pneumoniae* subsp. *pneumoniae* MGH 78578] | *Klebsiella pneumoniae* subsp. *Pneumoniae* |
| YP_005956057.1. NC_017540.1. | putative L-valine exporter [*Klebsiella pneumoniae* KCTC 2242] | *Klebsiella pneumoniae* |
| WP_020803764.1 | hypothetical protein [*Klebsiella pneumoniae*] | *Klebsiella pneumoniae* |
| WP_004114708.1 | branched-chain amino acid ABC transporter permease [*Klebsiella oxytoca*] | *Klebsiella oxytoca* |
| WP_004104783.1 | branched-chain amino acid ABC transporter permease [*Klebsiella oxytoca*] | *Klebsiella oxytoca* |
| WP_007370572.1 EJI92176.1 | branched-chain amino acid transport family protein [*Kosakonia radicincitans*] | *Kosakonia radicincitans* |
| EJI93105.1 | branched-chain amino acid transport family protein [*Enterobacter radicincitans* DSM 16656] | *Enterobacter radicincitans* |
| NP_668255.1 | hypothetical protein y0924 [*Yersinia pestis* KIM10+] | *Yersinia pestis* |
| YP_069399.1 | hypothetical protein YPTB0858 [*Yersinia pseudotuberculosis* IP 32953] | *Yersinia pseudotuberculosis* |
| YP_001479964.1 | hypothetical protein Spro_3740 [*Serratia proteamaculans* 568] | *Serratia proteamaculans* |
| WP_005189085.1 | branched-chain amino acid ABC transporter permease [*Yersinia intermedia*] | *Yersinia intermedia* |
| YP_004297213.1 | hypothetical protein YE105_C1014 [*Yersinia enterocolitica* subsp. *palearctica* 105.5R(r)] | *Yersinia enterocolitica* subsp. *Palearctica* |
| WP_019081388.1 | branched-chain amino acid ABC transporter permease [*Yersinia enterocolitica*] | *Yersinia enterocolitica* |
| WP_004392937.1 | branched-chain amino acid ABC transporter permease [*Yersinia kristensenii*] | *Yersinia kristensenii* |
| WP_016929852.1 | branched-chain amino acid ABC transporter permease [*Serratia marcescens*] | *Serratia marcescens* |
| WP_019845221.1 | branched-chain amino acid ABC transporter permease [*Dickeya zeae*] | *Dickeya zeae* |
| YP_003334824.1 | hypothetical protein Dd586_3285 [*Dickeya dadantii* Ech586] | *Dickeya dadantii* |
| YP_003042012.1. NC_012962.1. | conserved hypothetical protein [*Photorhabdus asymbiotica*] | *Photorhabdus asymbiotica* |
| WP_016941677.l | branched-chain amino acid ABC transporter permease [*Dickeya zeae*] | *Dickeya zeae* |
| WP_005275000.1 | branched-chain amino acid ABC transporter permease [*Yersinia bercovieri*] | *Yersinia bercovieri* |
| CAC44348.1 | YgaH protein [*Erwinia chrysanthemi*] | *Erwinia chrysanthemi* |
| WP_004704054.1 | branched-chain amino acid ABC transporter permease [*Yersinia aldovae*] | *Yersinia aldovae* |
| YP_003003218.1 | hypothetical protein Dd1591_0860 [*Dickeya zeae* Ech1591] | *Dickeya zeae* Ech1591 |
| WP_004707387.1 | branched-chain amino acid ABC transporter permease [*Yersinia frederiksenii*] | *Yersinia frederiksenii* |
| WP_008812527.1 | branched-chain amino acid ABC transporter permease [*Enterobacteriaceae bacterium* 9_2_54FAA] | *Enterobacteriaceae bacterium* |
| YP_008231813.1 | branched-chain amino acid ABC transporter permease [*Serratia liquefaciens* ATCC 27592] | *Serratia liquefaciens* |
| YP_051598.1 | hypothetical protein ECA3510 [*Pectobacterium atrosepticum* SCRI1043] | *Pectobacterium atrosepticum* |
| WP_019455592.1 | branched-chain amino acid ABC transporter permease [*Serratia marcescens*] | *Serratia marcescens* |
| YP_007407668.1 | putative amino acid transporter YgaH [*Serratia marcescens* WW4] | *Serratia marcescens* |

TABLE 2-continued

| YgaH homologous proteins | | |
|---|---|---|
| Acession Number | Name | Organism |
| WP_004716724.1 | branched-chain amino acid ABC transporter permease [*Yersinia rohdei*] | *Yersinia rohdei* |
| YP_003018880.1. NC_012917.1. | hypothetical protein PC1_3328 [*Pectobacterium carotovorum* subsp. *carotovorum* PC1] | *Pectobacterium carotovorum* subsp. *Carotovorum* |
| WP_004873539.1 | branched-chain amino acid ABC transporter permease [*Yersinia mollaretii*] | *Yersinia mollaretii* |
| WP_005975643.1 | branched-chain amino acid ABC transporter permease [*Pectobacterium wasabiae*] | *Pectobacterium wasabiae* |
| YP_003260828.1 | hypothetical protein Pecwa_3484 [*Pectobacterium wasabiae* WPP163] | *Pectobacterium wasabiae* |
| YP_002986522.1 | hypothetical protein Dd703_0892 [*Dickeya dadantii* Ech703] | *Dickeya dadantii* |
| YP_007345876.1 | Branched-chain amino acid transport protein (AzID) [*Serratia marcescens* FGI94] | *Serratia marcescens* |
| YP_004211502.1 | branched-chain amino acid transport [*Rahnella* sp. Y9602] | *Rahnella* sp. |
| YP_005400522.1 NC_017047.1. | putative L-valine exporter [*Rahnella aquatilis* HX2] | *Rahnella aquatilis* |
| WP_010305358.1 | branched-chain amino acid ABC transporter permease [*Pectobacterium carotovorum*] | *Pectobacterium carotovorum* |
| YP_003711584.1. NC_014228.1. | hypothetical protein XNC1_1314 [*Xenorhabdus nematophila* ATCC 19061] | *Xenorhabdus nematophila* |
| YP_006500219.1 AFN29790.1 | branched-chain amino acid transport [*Klebsiella oxytoca* E718] | *Klebsiella oxytoca* |
| EHT06521.1 | hypothetical protein HMPREF9690_03780 [*Klebsiella oxytoca* 10-5246] | *Klebsiella oxytoca* |
| EKP29342.1. | L-valine exporter [*Klebsiella oxytoca* M5aI] | *Klebsiella oxytoca* |
| EJK15417.1. | putative L-valine exporter [*Klebsiella pneumoniae* subsp. *pneumoniae* KPNIH18] | *Klebsiella pneumoniae* subsp. *Pneumoniae* |
| YP_006500219.1 | branched-chain amino acid transport [*Klebsiella oxytoca* E718] | *Klebsiella oxytoca* |
| BAH64805.1. | hypothetical protein KP1_4275 [*Klebsiella pneumoniae* subsp. *pneumoniae* NTUH-K2044]-ygaH | *Klebsiella pneumoniae* subsp. *Pneumoniae* |
| YP_003437996.1 | hypothetical protein Kvar_1056 [*Klebsiella variicola* At-22] | *Klebsiella variicola* |
| YP_003260828.1 | hypothetical protein Pecwa_3484 [*Pectobacterium wasabiae* WPP163] | *Pectobacterium wasabiae* |
| WP_010282658.1 | branched-chain amino acid ABC transporter permease [*Pectobacterium carotovorum*] | *Pectobacterium carotovorum* |
| YP_404405.1. NC_007606.1. ABB62914.1. | hypothetical protein SDY_2878 [*Shigella dysenteriae* Sd197] | *Shigella dysenteriae* |
| WP_000119748.1 | branched-chain amino acid ABC transporter permease [*Shigella dysenteriae*] | *Shigella dysenteriae* |
| YP_311672.1 AAZ89437.1 | hypothetical protein SSON_2827 [*Shigella sonnei* Ss046] | *Shigella sonnei* |
| WP_005150562.1 | putative membrane protein [*Shigella sonnei*] | *Shigella sonnei* |
| WP_000119744.1 | branched-chain amino acid ABC transporter permease [*Shigella boydii*] | *Shigella boydii* |
| WP_002427075.1 | branched-chain amino acid ABC transporter permease [*Yersinia pestis*] | *Yersinia pestis* |
| WP_017491438.1 | branched-chain amino acid ABC transporter permease [gamma proteobacterium WG36] | gamma proteobacterium |
| WP_002366138.1 | branched-chain amino acid transport family protein, partial [*Yersinia pestis*] | *Yersinia pestis* |

With accession number disclosed in the tables for each homolog the man skilled in the art is able to obtain the amino acid sequence and its nuceotidic coding sequence on NCBI databases for instance.

From the amino acid sequence or nucleotidic sequence, it is a routine task for the man skilled in the art to obtain genes encoding these homologues. It can be done either by artificial synthesis of the gene coding the protein of interest from its amino acid sequence or by PCR amplification of the coding region of interest from the corresponding genomic DNA. In the context of the invention, these genes are called “ygaZ or ygaH homologous genes”. The sequences of these ygaZH homologous genes may be adjusted to the codon bias of the host microorganism.

In a specific embodiment of the invention, the recombinant microorganism overexpresses the genes ygaZ and ygaH from *E. coli* coding the proteins whose sequences are respectively disclosed in SEQ ID NO: 1 and SEQ ID NO: 2 or brnF and brnE from *C. glutamicum* or their homologous genes. Preferably, ygaZ and ygaH homologous genes are composed by the gene pair originating from the same organism and composed by the homologous gene of ygaZ and the homologous gene of ygaH. However mismatch pair of an ygaZ homologous gene from a first organism and an ygaH homologous gene from a second organism could be used. Preferably, the genes ygaZH, brnFE or their homologous genes are overexpressed.

YgaZH homologous genes are chosen among genes encoding the YgaZ and YgaH homologues disclosed respectively in table 1 and in table 2. Preferably, ygaZH homologous genes are chosen among genes encoding YgaZH homologues from *Citrobacter* species, *Shigella* species, *Raoultella* species, *Enterobacter* species, *Yersinia* species and *Photorhabdus* species. More preferably ygaZH homologous genes originate from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii*. Most preferably, ygaZH homologous genes originate from *Citrobacter koseri, Citrobacter* youngae, *Citrobacter freundii* or *Enterobacter* sp. Therefore, ygaZH homologous genes are preferably chosen among genes coding the pair of YgaZ homolog and YgaH homolog defined respectively by: SEQ ID NO: 3 and SEQ ID NO: 4 from *Citrobacter koseri*, SEQ ID NO: 5 and SEQ ID NO: 6 from *Shigella flexneri*, SEQ ID NO: 7 and SEQ ID NO: 8 from *Raoultella ornithinolytica*, SEQ ID NO: 9 and SEQ ID NO: 10 from *Enterobacter* sp. (R4-368), SEQ ID NO: 11 or 12 and SEQ ID NO: 13 or 14 from *Yersinia enterocolitica* subsp. *enterocolitica*, SEQ ID NO: 15 and SEQ ID NO: 16 from *Photorhabdus luminescens* subsp. *laumondii*, SEQ ID NO: 17 and SEQ ID NO: 18 from *Citrobacter youngae*, SEQ ID NO: 19 and SEQ ID NO: 20 from *Citrobacter freundii.*

In a preferred embodiment of the invention, these genes ygaZH or brnFE or homologous genes originating from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii* are overexpressed under the control of an inducible promoter. The man skilled in the art knows such inducible promoters. For instance, promoters like $\lambda P_R$ or $\lambda P_L$ may be used to overexpress ygaZH genes or brnFE genes or ygaZH homologous genes originating from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii* in the recombinant microorganism of the invention.

It is another object of the invention to identify ygaZH homologous genes and to overexpress said genes in amino-acid producer microorganism, alone or in combination with other genetic modifications as disclosed below.

Optimisation of Methionine Biosynthesis Pathway

The recombinant microorganism according to the invention is modified for improving the production of methionine. Genes involved in methionine production are well known in the art, and comprise genes involved in the methionine specific biosynthesis pathway as well as genes involved in precursor-providing pathways and genes involved in methionine consuming pathways.

Efficient production of methionine requires the optimisation of the methionine specific pathway and several precursor—providing pathways. Methionine producing strains have already been described, in particular in patent applications WO2005/111202, WO2007/077041 and WO2009/043803. These applications are incorporated as reference into this application.

Except otherwise stated, all the genes mentioned below concerning optimisation of methionine biosynthesis pathway are referring to those from *E. coli.*

In a specific embodiment of the invention, the recombinant microorganism is modified as described below: the expression of at least one gene chosen among ptsG, pyc, pntAB, cysP, cysU, cysW, cysA, cysM, cysJ, cysI, cysH, gcvT, gcvH, gcvP, lpd, serA, serB, serC, cysE, metF, metA, metA* allele encoding for an enzyme with reduced feed-back sensitivity to S-adenosylmethionine and/or methionine, thrA, and thrA* allele encoding for an enzyme with reduced feed-back inhibition to threonine is increased.

- ptsG encodes the PTS enzyme $IICB^{Glc}$ as described in patent application WO2013/001055,
- pyc encodes a pyruvate carboxylase as described in patent application WO2013/001055. In a preferred embodiment, the pyc gene is heterologous and is chosen from pyc genes from *Rhizobium etli, Bacillus subtilis, Lactococcus lactis, Pseudomonas fluorescens* or *Corynebacterium* species,
- pntAB encode subunits of a membrane-bound transhydrogenase, such as described in patent application WO2012/055798,
- cysP encodes a periplasmic sulphate binding protein, as described in WO2007/077041 and in WO2009/043803,
- cysU encodes a component of sulphate ABC transporter, as described in WO2007/077041 and in WO2009/043803,
- cysW encodes a membrane bound sulphate transport protein, as described in WO2007/077041 and in WO2009/043803,
- cysA encodes a sulphate permease, as described in WO2007/077041 and in WO2009/043803,
- cysM encodes an O-acetyl serine sulfhydralase, as described in WO2007/077041 and in WO2009/043803,
- cysI and cysJ encode respectively the alpha and beta subunits of a sulfite reductase as described in WO2007/077041 and in WO2009/043803. Preferably cysI and cysJ are overexpressed together,
- cysH encodes an adenylylsulfate reductase, as described in WO2007/077041 and in WO2009/043803.

Increasing C1 metabolism is also a modification that leads to improved methionine production. It relates to the increase of the activity of at least one enzyme involved in the C1 metabolism chosen among GcvTHP, Lpd, MetF or MetH. In a preferred embodiment of the invention, the one carbon metabolism is increased by enhancing the expression and/or the activity of at least one of the following:

gcvT, gcvH, gcvP, and lpd, coding for the glycine cleavage complex, as described in patent application WO 2007/077041. The glycine-cleavage complex (GCV) is a multienzyme complex that catalyzes the oxidation of glycine, yielding carbon dioxide, ammonia, methylene-THF and a reduced pyridine nucleotide. The GCV complex consists of four protein components, the glycine dehydrogenase said P-protein (GcvP), the lipoyl-GcvH-protein said H-protein (GcvH), the aminomethyltransferase said T-protein (GcvT), and the dihydrolipoamide dehydrogenase said L-protein (GcvL or Lpd). P-protein catalyzes the pyridoxal phosphate-dependent liberation of CO2 from glycine, leaving a methylamine moiety. The methylamine moiety is transferred to the lipoic acid group of the H-protein, which is bound to the P-protein prior to decarboxylation of glycine. The T-protein catalyzes the release of NH3 from the methylamine group and transfers the remaining C1 unit to THF, forming methylene-THF. The L protein then oxidizes the lipoic acid component of the H-protein and transfers the electrons to $NAD^+$, forming NADH;

MetF encoding a methylenetetrahydrofolate reductase, as described in patent application WO2007/07704.

The overexpression of at least one of the following genes involved in serine biosynthesis also reduces the production of the by-product isoleucine:

serA which encodes a phosphoglycerate dehydrogenase, as described in WO2007/077041 and in WO2009/043803, serB which encodes a phosphoserine phosphatase, as described in WO2007/077041 and in WO2009/043803, serC which encodes a phosphoserine aminotransferase, as described in WO2007/077041 and in WO2009/043803.

The overexpression of the following genes has already been shown to improve the production of methionine:

cysE encodes a serine acyltransferase; its overexpression allows an increase in methionine production, as described in WO2007/077041;

metA encodes a homoserine succinyltransferase. The allele metA* codes for an enzyme with reduced feed-back sensitivity to S-adenosylmethionine and/or methionine. Preferentially, the allele metA* described in the patent application WO2005/111202 is used;

thrA encodes an aspartokinase/homoserine dehydrogenase; the thrA* allele codes for an enzyme with reduced feed-back inhibition to threonine, as described in WO2005/111202.

In a specific embodiment of the invention, at least one of said genes is under control of an inducible promoter. In a preferred embodiment of the invention, at least one of these genes is under the control of a temperature inducible promoter. Preferably, the expression of at least one of the genes: thrA, cysE, metA, is under the control of an inducible promoter, directly or indirectly. More preferably, the genes thrA, cysE and metA are under control of an inducible promoter, directly or indirectly. In a preferred embodiment of the invention, expression of thrA gene is under direct control of an inducible promoter and expression of cysE gene is under polar effect of inducible expression of thrA gene. In another preferred embodiment of the invention, expression of thrA gene is under direct control of an inducible promoter and expressions of cysE and metA genes are under polar effect of inducible expression of thrA gene.

In a most preferred embodiment, the temperature inducible promoter belongs to the family of $P_R$ promoters. A methionine producing strain having genes under control of inducible promoters is described in patent application WO2011/073122.

In another specific embodiment of the invention, the microorganism has been further modified, and the expression of at least one of the following genes is attenuated: metJ, pykA, pykF, purU, ybdL, yncA, metE, dgsA, metN, metI, metQ or udhA.

The gene metJ codes for the repressor protein MetJ (GenBank 1790373), responsible for the down-regulation of the methionine regulon as was suggested in patent application JP2000/157267, The genes pykA and pykF code for the enzymes ‘pyruvate kinase’. The attenuation of the expression of at least one or both of the pyruvate kinases decreases the consumption of phosphoenol pyruvate (PEP). Increased availability of PEP can increase the production of oxaloacetate, an important precursor of aspartate, which in turn is a precursor of methionine, as described in WO2007/077041 and in WO2009/043803, purU codes for a formyltetrahydrofolate deformylase, an enzyme that catalyzes the formyl-THF deformylase reaction. The attenuation of the deformylase activity increases the production of methyl-THF that is required for methylation of homocysteine. Loss of C1 metabolites by deformylation leads to an increased production of homocysteine that cannot be transformed into methionine. Homocysteine can then be a substrate for the enzyme cystathionine gamma synthase (MetB) that can catalyze the reaction between 0-succinylhomoserine and homocysteine resulting in the production of homolanthionine, as described in WO2007/077041 and in WO2009/043803, ybdL encodes an aminotransferase as described in patent application WO2012/090021, yncA encodes a N-acyltransferase, as described in patent application WO2010/020681, metE encodes a cobalamin-independent methionine synthase, as described in patent application PCT/IB2012/001336, dgsA, better known as Mlc, encodes a transcriptional dual regulator that controls the expression of genes encoding enzymes of the phosphotransferase (PTS) and phosphoenolpyruvate (PEP) systems as described in patent application WO2013/001055, metN, metI, metQ, encode a methionine uptake system, udhA encodes soluble pyridine nucleotide transhydrogenase, as described in patent application WO2012/055798.

In a more preferred embodiment of the invention, the fermentative production of methionine and/or its derivatives by a recombinant microorganism, wherein the methionine import is attenuated and the methionine efflux is enhanced, from glucose as a main carbon source, may be achieved through a combination of the above discussed modifications in said microorganism, for example:

the expression of the gene metJ is attenuated and the expression of a metA* allele encoding for an enzyme with reduced feed-back sensitivity to S-adenosylmethionine and/or methionine (MetA*) is enhanced;

the expression of the gene metJ is attenuated; the expression of a metA* allele encoding for an enzyme with reduced feed-back sensitivity to S-adenosylmethionine and/or methionine (MetA*) is enhanced; and the expression of a thrA* allele encoding for an enzyme with reduced feed-back inhibition to threonine (thrA*) is enhanced;

- the expression of the gene metJ is attenuated; the expression of a metA* allele encoding for an enzyme with reduced feed-back sensitivity to S-adenosylmethionine and/or methionine (MetA*) is enhanced; the expression of a thrA* allele encoding for an enzyme with reduced feed-back inhibition to threonine (thrA*) is enhanced; and the expression of the gene cysE is enhanced;
- the expression of the gene metJ is attenuated; the expression of a metA* allele encoding for an enzyme with reduced feed-back sensitivity to S-adenosylmethionine and/or methionine (MetA*) is enhanced; the expression of a thrA* allele encoding for an enzyme with reduced feed-back inhibition to threonine (thrA*) is enhanced; the expression of the gene cysE is enhanced; and the expression of the genes metF is enhanced.

In a particular aspect of the invention, the recombinant microorganism comprises the following genetic modifications:

- the genes metH, and fldA and fpr from *E. coli* or their homologous genes from *C. glutamicum* are overexpressed,
- the genes ygaZ and ygaH from *E. coli* or the genes brnF and brnE from *C. glutamicum* or their homologous genes originating from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii* are overexpressed,
- the expression of the genes metA*, cysPUWAM, cysJIH, gcvTHP, metF, serA, serB, serC, cysE, thrA*, ptsG and pyc are enhanced, and
- the expression of genes metJ, pykA, pykF, purU, metE, dgsA and yncA are attenuated.

In a particular embodiment of the invention, the microorganism to be modified is from the bacterial family Enterobacteriaceae or Corynebacteriaceae.

Preferentially, the microorganism to be modified is *Escherichia coli* or *Corynebacterium glutamicum.*

Culture Conditions

In a second aspect of the invention, a method is optimised for the fermentative production of methionine and/or its derivatives. It comprises the followings steps:

- Culturing a recombinant microorganism wherein the cobalamin-dependent methionine synthase activity and the methionine efflux are enhanced by overexpressing respectively the genes metH, and optionally the genes fldA and fpr genes from *E. coli* or their homologous genes from *C. glutamicum* and the genes ygaZH from *E. coli* or the genes brnFE from *C. glutamicum* or their homologous genes in an appropriate culture medium comprising a fermentable source of carbon and a source of sulphur, and,
- Recovering methionine and/or its derivatives from the culture medium.

Those skilled in the art are able to define the culture conditions for the microorganisms according to the invention. In particular the bacteria are fermented at a temperature between 20° C. and 55° C., preferentially between 25° C. and 40° C., and more specifically about 30° C. for *C. glutamicum* and about 37° C. for *E. coli.*

For *E. coli*, the culture medium can be of identical or similar composition to an M9 medium (Anderson, 1946), an M63 medium (Miller, 1992); or a medium such as defined by Schaefer et al., (1999).

For *C. glutamicum*, the culture medium can be of identical or similar composition to BMCG medium (Liebl et al., 1989) or to a medium such as described by Riedel et al., (2001).

In the method of the invention, the ygaZH homologous genes which are overexpressed in the recombinant microorganism are preferably chosen among the group consisting in homologous genes from *Citrobacter* species, *Shigella* species, *Raoultella* species, *Enterobacter* species, *Yersinia* species and *Photorhabdus* species, and more preferably originate from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii.*

In a specific embodiment of the method, the recombinant microorganism comprises the following genetic modifications:

a. overexpression of the genes metH, and fldA and fpr from *E. coli*, or their homologous genes from *C. glutamicum* and
b. overexpression of the genes ygaZH from *E. coli*, or brnFE from *C. glutamicum* or their homologous genes.

In this specific embodiment of the invention, said ygaZH homologous genes are preferably chosen among the group consisting in homologous genes from *Citrobacter* species, *Shigella* species, *Raoultella* species, *Enterobacter* species, *Yersinia* species and *Photorhabdus* species, and more preferably chosen among the groups consisting in homologous genes from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii.*

In the method of the invention, the ygaZH homologous genes which are overexpressed in the recombinant microorganism are most preferably originating from *Citrobacter koseri, Citrobacter youngae, Citrobacter freundii* or *Enterobacter* sp.

In some embodiment of the invention, the growth of the recombinant microorganism is subjected to a limitation or starvation/deficiency for one or several inorganic substrate, in particular phosphate and/or potassium, in the culture medium. It refers to condition under which growth of the microorganisms is governed by the quantity of an inorganic chemical supplied that still permits weak growth. Such limitation in microorganism growth has been described in the patent application WO2009/043372. In a preferred embodiment of the invention, the culture is subjected to phosphate limitation.

The action of "recovering methionine and/or its derivatives from the culture medium" designates the action of recovering L-methionine and/or one of its derivatives, in particular N-acetyl methionine (NAM) and S-adenosyl methionine (SAM) and all other derivatives that may be useful such as hydroxy-methionine (or methionine hydroxy analogue or MHA). The methods for the recovery and purification of the produced compounds are well known to those skilled in the art (see in particular WO2005/007862, WO2005/059155). Preferably, the step of recovering methionine and/or its derivatives comprises a step of concentration of methionine and/or its derivatives in the fermentation broth.

The amount of product in the fermentation medium can be determined using a number of methods known in the art, for example, high performance liquid chromatography (HPLC) or gas chromatography (GC). For example the quantity of methionine obtained in the medium is measured by HPLC after OPA/Fmoc derivatization using L-methionine (Fluka, Ref 64319) as a standard. The amount of NAM is determinated using refractometric HPLC using NAM (Sigma, Ref 01310) as a standard.

EXAMPLES

The following experiments demonstrate how overexpression of genes encoding for the L-methionine excretion system together with the overexpression of genes encoding for the B12-dependent methionine synthase and its reactivation system in microorganisms such as *E. coli* and *C. glutamicum* improved methionine production.

In the examples given below, methods well known in the art were used to construct *E. coli* and *C. glutamicum* strains containing replicating vectors and/or various chromosomal insertions, deletions, and substitutions using homologous recombination well described by Datsenko & Wanner, (2000) for *E. coli* and in patent WO2007012078 for *C. glutamicum.*

In the same manner, the use of plasmids or vectors to express or overexpress one or several genes in a recombinant microorganisms are well known by the man skilled in the art.

Examples of suitable *E. coli* expression vectors include pTrc, pACYC184n pBR322, pUC18, pUC19, pKC30, pRep4, pHS1, pHS2, pPLc236 etc. . . . .

Examples of suitable *C. glutamicum* and *E. coli* shuttle vectors are e. g. pClik5aMCS (WO2005059093) or can be found in Eikmanns et al., (1991).

Examples for suitable vectors to manipulate Corynebacteria can be found in the handbook of Corynebacteria edited by Eggeling and Bott in 2005.

Protocols

Several protocols have been used to construct methionine producing strains described in the following examples.

Protocol 1 (Chromosomal modifications by homologous recombination, selection of recombinants and antibiotic cassette excision) and protocol 2 (Transduction of phage P1) used in this invention have been fully described in patent application WO2013/001055.

Protocol 3: Construction of Recombinant Plasmids

Recombinant DNA technology is well described and known by the man skilled in the art.

Briefly, the DNA fragments are PCR amplified using oligonucleotides (the person skilled in the art will is able to design) and MG1655 genomic DNA as matrix. The DNA fragments and selected plasmid are digested with compatible restriction enzymes, ligated and then transformed in competent cells. Transformants are analysed and recombinant plasmids of interest are verified by DNA sequencing.

TABLE 3

Sequences cited in the following examples

| SEQ ID NO | Sequence 5' → 3' |
|---|---|
| 21 | AACACTGCAAAATCCTGCTATTTGATTTGTATGAGTGATA AGTGTAACGCCGAATAATCGTCGTTGGCGAATTTTACGAC TCTGACAGGAGGTGGCAATG |
| 22 | GAGAAAGTAAACGTAACATGATGACGACAATTCTGACGAT TCATGTTCCTTCAACGCCGGGGCGCGCATGGAATATGCTG GTGGCACTTCAGGCAGGAAA |
| 23 | TGAGGAATAGACAATGTTAGTTAGTAAAAGCAACGGATTT AACGCTAGCGCAGTTTTGGGTAGTGGAAGTTATAATGAAA ATAAATCTTCTAAACACATG |
| 24 | TGCGCTAAAAGAAATGAATAGAACCTTTTCGATAATATAA GAAAAAGTGATTTTCATGTTGGTTTACTTAAGCCAAGTAG TACGCGTAGTGTTATTTTAG |
| 25 | AAATTATTCTTGTATCTTTGTTATAATATGGGAAAGTGCA ACCAT |
| 26 | CGTTAATCAGCAGGTTAGCCAGCCACAAAAAGCCATTGAG AAAATTATTGATTTTACATGGGATTATTATATTGCTAATC CTTGGTTTTTAAAAATTGTG |
| 27 | TCATCTACCGCGCACGAATAAAACTGCCATCCGGCTGGCG GGTGAACAGGACCTGTTGATTATTCCCCGTATCAATGGTT AAGCCCGTCACCACGCCGCT |

Example 1: Overproduction of the Cobalamin-Dependent Methionine Synthase or Overproduction of a L-Methionine Secretion System in a L-Methionine Overproducer *E. coli* Recombinant Strain—Strain 1 and Construction of Strains 2, 3, 4, 5 and 6

Strain 1—Reference Strain

Methionine producing strain 17 described in patent application WO2013/001055 (which is incorporated as reference into this application) was renamed strain 1 in this present application. For reminder this strain overexpressed metH owing artificial promoter and ribosome binding site integrated in front of metH gene at its endogenous locus (for details see as patent application WO2007/077041). This strain contains also the mutation in metE gene disclosed in patent application WO2013/190343.

Construction of Strain 5—Overproduction of the Cobalamin-Dependent Methionine Synthase, Overexpression of metH, fldA and Fpr The *E. coli* gene encoding the cobalamin-dependent methionine synthase, metH and genes fldA and fpr encoding for the reactivation system of MetH, were all overexpressed in genetic background of strain 1.

Before using strain 1, the antibiotic cassette was removed from ΔdgsA modification using the Flp recombinase as described by Datsenko & Wanner, 2000 (according to Protocol 1).

The kanamycin sensible transformants were selected and the absence of antibiotic cassette at ΔdgsA locus was verified by a PCR analysis with appropriate oligonucleotides. The strain retained was designated strain 2.

To overexpress metH, this gene, operatively linked to the same promoter and ribosome binding site as described in patent application WO2007/077041 was integrated on the chromosome at two different loci ybeM and ypjC (selected from the list disclosed in the patent application WO2011/073122 and whose deletion do not have impact on methionine production).

To strongly overexpress metH, the homologous recombination strategy described by Datsenko & Wanner, 2000 (according to Protocol 1) was used. For both chromosomal integrations, a fragment carrying metH gene linked to its artificial promoter and a resistance marker both flanked by DNA sequences homologous to the targeted integration locus ybeM or ypjC was PCR amplified by the overlapping PCR technique (overlapping oligonucleotides). The sequences for recombination into ybeM and ypjC are referred as SEQ ID NO 21 and 22, and SEQ ID NO 23 and 24 (listed in table 3), for ybeM and ypjC respectively. The PCR products "ΔybeM::metH::Km" and "ΔypjC::metH::Cm" obtained were then introduced by electroporation into the strain MG1655 metA*11 (pKD46), separately. The antibiotic resistant transformants were selected and the insertion of the metH gene with the resistance cassette at the targeted locus was verified by a PCR analysis with appropriate oligonucleotides. The strains retained were designated MG1655 metA*11 ΔybeM::metH::Km and MG1655 metA*11 ΔypjC::metH::Cm. Finally, the ΔybeM::metH::Km and ΔypjC::metH::Cm chromosomal integrations were transferred by P1 phage transduction successively (according to Protocol 2) from the MG1655 metA*11 ΔybeM::metH::Km and MG1655 metA*11 ΔypjC::metH to strain 2. Chloramphenicol or kanamycin resistant transductants were selected and the presence of ΔybeM::metH::Km and ΔypjC::metH::Cm chromosomal integrations were verified by a PCR analysis with appropriate oligonucleotides. The strain retained was called strain 3.

The antibiotic cassettes were removed from chromosomal integrations made at ybeM and ypjC loci into strain 3 using the Flp recombinase as described by Datsenko & Wanner, 2000 (according to Protocol 1). The kanamycin and chloramphenicol sensible transformants were selected and the absence of antibiotic cassette at both loci was verified by a PCR analysis with appropriate oligonucleotides. The strain retained was designated strain 4.

To overexpress fldA and fpr, these genes, were operatively linked to artificial promoters and to artificial ribosome binding site and were integrated onto the chromosome at the ytfA locus (same selection criteria as ybeM and ypjC loci, see above). The artificial promoters were constructed with SEQ ID NO 25 for fldA and as described for the overexpression of cysPUWAM operon in patent application WO2009/043803 for fpr. The artificial ribosome binding sites are the same as described to overexpress ptsG gene in strain 17 disclosed in patent application WO2013/001055.

To add copies of fldA and fpr overexpression onto the chromosome, the homologous recombination strategy described by Datsenko & Wanner, 2000 (according to Protocol 1) was used. A fragment carrying fldA and fpr genes, with their respective promoters, and a resistance marker, both flanked by DNA sequence homologous to the integration locus ytfA was PCR amplified by overlapping PCR technique (overlapping oligonucleotides). The sequences for recombination into the ytfA locus are referred as SEQ ID NO 26 and 27 (listed in table 3). The PCR product "ΔytfA::fldA-fPr::Km" obtained was then introduced by electroporation into the MG1655 metA*11 (pKD46) strain. The antibiotic resistant transformants were then selected and the insertion of the fldA-fpr genes with the resistance cassette at the ytfA locus was verified by a PCR analysis with appropriate oligonucleotides.

The strain retained was designated MG1655 metA*11 ΔytfA::fldA-fpr::Km. Finally, the ΔytfA::fldA-fpr::Km chromosomal integration was transferred by P1 phage transduction (according to Protocol 2) from the MG1655 metA*11 ΔytfA::fldA-fpr::Km to strain 4. Kanamycin resistant transductants were selected and the presence of ΔytfA::fldA-fpr::Km chromosomal integration was verified by a PCR analysis with appropriate oligonucleotides. The strain retained was called strain 5.

Construction of Strain 6—Overproduction of a L-Methionine Secretion System, Overexpression of ygaZH The *E. coli* genes ygaZH encoding the exporter of methionine were overexpressed in strain 1. They were cloned on the moderate plasmid copy number pCL1920 (Lerner & Inouye, 1990) with the use of the natural promoter of ygaZ. This plasmid was named pME1247. Finally, the plasmid pME1247 was transformed into strain 1, giving the strain 6.

Example 2: Overproduction of the Cobalamin-Dependent Methionine Synthase and Overproduction of a L-Methionine Secretion System in a L-Methionine Overproducer *E. coli* Strain—Construction of Strain 7

The *E. coli* genes ygaZH encoding the exporter of methionine, were overexpressed in strain 5. The plasmid pME1247 was transformed into strain 5, giving rise to strain 7.

Example 3: Overproduction of the Cobalamin-Dependent Methionine Synthase or its Reactivation System or Overproduction of a L-Methionine Secretion System in a L-Methionine Overproducer *C. glutamicum* Recombinant Strain—Construction of Strains A to F The *C. glutamicum* strain ATCC 13032 hom* ask* metH (designated strain A in the following) is described in patent WO2007/012078.

In that strain A, hom* and ask* correspond to feedback resistant alleles of homoserine dehydrogenase encoding the protein Hsdh S393F and of aspartate kinase encoding the protein Ask T311I also called LysC T311I, respectively.

This strain A is subsequently mutagenized with N-Methyl-N'-nitroguanidine as described in patent WO2007/012078. Clones that show a methionine titer that is at least twice that in strain A are isolated. One such clone, used in further experiments, is named strain B. This strain B is a *C. glutamicum* L-methionine producer.

Then, the *C. glutamicum* strain B is modified as described in patents WO2007/012078 and WO2004/050694 to obtain the strain C including hsk* metY metA metF DmcbR.

The mutated allele hsk* encoding the homoserine kinase Hsk T190A is overexpressed as well as metY encoding the O-acetylhomoserine sulfhydrylase, metA encoding the homoserine acetyl-transferase, metF encoding the homocysteine methylase and mcbR gene is deleted.

In order to increase the cobalamin-dependent methionine synthase activity in *C. glutamicum* L-methionine producer strain C, metHcg (metH gene from *C. glutamicum*) is overexpressed together with fprA1 gene encoding a ferredoxin reductase working as MetH reoxidation protein. These modifications are performed according the description of patent WO2009/144270. The resulting strain is called strain D.

Another way to increase the cobalamin-dependent methionine synthase activity in *C. glutamicum* L-methionine producer strain C, is to overexpress metHEc (metH gene from *E. coli*) together with fldA and fpr genes from *E. coli* encoding the flavodoxins involved into the reactivation of MetH enzyme. This is achieved according to the description of patent WO2009/144270. The resulting strain is called strain E.

In order to increase the L-methionine excretion system specific of *C. glutamicum* in strain C, the brnFE operon is overexpressed from the *E. coli*-*C. glutamicum* shuttle expression vector pEC-XT99A (EP1085094). The plasmid was constructed in *E. coli* from PCR-generated fragments by using *C. glutamicum* ATCC 13032 DNA as a template. The plasmid was constructed as described by Trotschel et al., (2005) in pEC-XT99A, and the resulting plasmid pCB1 is subsequently transformed into strain C giving rise to strain F.

Example 4: Combined Overproduction of the Cobalamin-Dependent Methionine Synthase with the Overproduction of a L-Methionine Secretion System in a *C. glutamicum* L-Methionine Overproducer Strain—Construction of Strains G and H In order to combine the overproduction of $MetH_{CG}$, FprA1 or $MetH_{EC}$, FldA, Fpr in *C. glutamicum* with the overproduction of the specific L-methionine excretion system BrnFE, the plasmid pCB1 described above is introduced by electroporation into strains D and E giving rise to strains G and H respectively.

Strain G carries only genes belonging to *C. glutamicum* whereas strain H carries the cobalamin-dependent methionine synthase and its reactivation system from *E. coli.*

The exporter is in all cases BrnFE.

Example 5: Production of L-Methionine by Fermentation in Bio-Reactor with *E. coli* Strains Strains described in previous examples were tested under production conditions in 2.5 L reactors (Pierre Guerin) using a fedbatch strategy.

Briefly, an 24 hours culture grown in 10 mL LB medium with 2.5 $g \cdot L^{-1}$ glucose was used to inoculate a 24 hours preculture in minimal medium (B1a). These incubations were carried out in 500 mL baffled flasks containing 50 mL of minimal medium (B1a) in a rotary shaker (200 RPM). The first preculture was realized at a temperature of 30° C., the second one at a temperature of 34° C.

A third preculture step was carried out in bio-reactors (Sixfors) filled with 200 mL of minimal medium (Bib) inoculated to a biomass concentration of 1.2 $g \cdot L^{-1}$ with 5 mL concentrated preculture. The preculture temperature was maintained constant at 34° C. and the pH was automatically adjusted to a value of 6.8 using a 10% $NH_4OH$ solution. The dissolved oxygen concentration was continuously adjusted to a value of 30% of the partial air pressure saturation with air supply and/or agitation. After glucose exhaustion from the batch medium, the fedbatch was started with an initial flow rate of 0.7 $mL \cdot h^{-1}$, before increasing exponentially for 26 hours with a growth rate of 0.13 If' in order to obtain a final cellular concentration of about 20 $g \cdot L^{-}$.

TABLE 4

Preculture batch mineral medium composition (B1a and B1b)

| Compound | B1a Concentration ($g \cdot L^{-1}$) | B1b Concentration ($g \cdot L^{-1}$) |
|---|---|---|
| $Zn(CH_3COO)_2 \cdot 2H_2O$ | 0.0130 | 0.0130 |
| $CuCl_2 \cdot 2H_2O$ | 0.0015 | 0.0015 |
| $MnCl_2 \cdot 4H_2O$ | 0.0150 | 0.0150 |
| $CoCl_2 \cdot 6H_2O$ | 0.0025 | 0.0025 |
| $H_3BO_3$ | 0.0030 | 0.0030 |
| $Na_2MoO_4 \cdot 2H_2O$ | 0.0025 | 0.0025 |
| Fe(III) citrate $H_2O$ | 0.1064 | 0.1064 |
| EDTA | 0.0084 | 0.0084 |
| $MgSO_4 \cdot 7H_2O$ | 1.00 | 1.00 |
| $CaCl_2 \cdot 2H_2O$ | 0.08 | 0.08 |

TABLE 4-continued

Preculture batch mineral medium composition (B1a and B1b)

| Compound | B1a Concentration ($g \cdot L^{-1}$) | B1b Concentration ($g \cdot L^{-1}$) |
|---|---|---|
| Citric acid | 1.70 | 1.70 |
| $KH_2PO_4$ | 4.56 | 4.56 |
| $K_2HPO_4 \cdot 3H_2O$ | 2.53 | 2.53 |
| $(NH_4)_2HPO_4$ | 1.11 | 1.11 |
| $(NH_4)_2SO_4$ | 4.90 | 4.90 |
| $(NH_4)_2S_2O_3$ | 1.00 | 1.00 |
| Thiamine | 0.01 | 0.01 |
| Vitamin B12 | 0.01 | 0.01 |
| Glucose | 30.00 | 5.00 |
| MOPS | 30.00 | 0.00 |
| $NH_4OH$ 28% | Adjusted to pH 6.8 | Adjusted to pH 6.8 |

TABLE 5

Preculture fedbatch mineral medium composition (F1)

| Compound | Concentration ($g \cdot L^{-1}$) |
|---|---|
| $Zn(CH_3COO)_2 \cdot H_2O$ | 0.0104 |
| $CuCl_2 \cdot 2H_2O$ | 0.0012 |
| $MnCl_2 \cdot 4H_2O$ | 0.0120 |
| $CoCl_2 \cdot 6H_2O$ | 0.0020 |
| $H_3BO_3$ | 0.0024 |
| $Na_2MoO_4 \cdot 2H_2O$ | 0.0020 |
| Fe(III) citrate $H_2O$ | 0.0524 |
| EDTA | 0.0067 |
| $MgSO_4$ | 5.00 |
| $(NH_4)_2SO_4$ | 8.32 |
| $Na_2SO_4$ | 8.95 |
| $(NH_4)_2S_2O_3$ | 24.80 |
| Thiamine | 0.01 |
| Glucose | 500.00 |
| Vitamin B12 | 0.01 |
| $NH_4OH$ 28% | Adjusted to pH 6.8 |

Subsequently, 2.5 L fermentors (Pierre Guerin) were filled with 600 or 620 mL of minimal medium (B2) and were inoculated to a biomass concentration of 3.2 $g \cdot L^{-1}$ with a preculture volume ranging between 80 to 100 mL.

Cell growth is controlled by phosphate, that is why the final phosphate concentration in batch medium B2 was adjusted to a value comprised between 0 to 20 mM, by addition of different concentrations of $KH_2PO_4$, $K_2HPO_4$ and $(NH_4)_2HPO_4$. In the same manner, the final phosphate concentration of F2 medium was adjusted to a value comprise between 5 to 30 mM, by addition of different concentrations of $KH_2PO_4$, $K_2HPO_4$ and $(NH_4)_2HPO_4$. Thiosulfate concentration in fedbatch medium can be adjusted in order to prevent a starvation of this compound during the culture.

TABLE 6

Culture batch mineral medium composition (B2)

| Compound | Concentration ($g \cdot L^{-1}$) |
|---|---|
| $Zn(CH_3COO)_2 \cdot 2H_2O$ | 0.0130 |
| $CuCl_2 \cdot 2H_2O$ | 0.0015 |
| $MnCl_2 \cdot 4H_2O$ | 0.0150 |
| $CoCl_2 \cdot 6H_2O$ | 0.0025 |
| $H_3BO_3$ | 0.0030 |
| $Na_2MoO_4 \cdot 2H_2O$ | 0.0025 |
| Fe(III) citrate $H_2O$ | 0.1064 |
| EDTA | 0.0084 |
| $MgSO_4 \cdot 7H_2O$ | 1.00 |
| $CaCl_2 \cdot 2H_2O$ | 0.08 |
| Citric acid | 1.70 |
| $(NH_4)_2S_2O_3$ | 7.74 |

TABLE 6-continued

| Culture batch mineral medium composition (B2) | |
|---|---|
| Compound | Concentration ($g \cdot L^{-1}$) |
| Thiamine | 0.01 |
| Vitamin B12 | 0.01 |
| Biotin | 0.10 |
| Glucose | 10 |
| $NH_4OH$ 28% | Adjusted to pH 6.8 |
| IPTG | 0.0047 |

TABLE 7

| Culture fedbatch medium composition (F2) | |
|---|---|
| Compound | Concentration ($g \cdot L^{-1}$) |
| $Zn(CH_3COO)_2 \cdot 2H_2O$ | 0.0104 |
| $CuCl_2 \cdot 2H_2O$ | 0.0012 |
| $MnCl_2 \cdot 4H_2O$ | 0.0120 |
| $CoCl_2 \cdot 6H_2O$ | 0.0020 |
| $H_3BO_3$ | 0.0024 |
| $Na_2MoO_4 \cdot 2H_2O$ | 0.0020 |
| Fe(III) citrate $H_2O$ | 0.0524 |
| EDTA | 0.0067 |
| $MgSO_4$ | 5.00 |
| $(NH_4)_2S_2O_3$ | 60.00 |
| Thiamine | 0.01 |
| Vitamin B12 | 0.01 |
| Biotin | 0.10 |
| Glucose | 500 |
| IPTG | 0.0047 |

The culture temperature was maintained constant at 37° C. and pH was maintained to the working value (6.8) by automatic addition of $NH_4OH$ solutions (10% and 28%). The initial agitation rate was set at 200 RPM during the batch phase and was increased up to 1000 RPM during the fedbatch phase. The initial airflow rate was set at 40 $NL \cdot h^1$ during the batch phase and was augmented to 100 $NL \cdot h^1$ at the beginning of the fedbatch phase. The dissolved oxygen concentration was maintained at values between 20 and 40%, preferentially 30% saturation by increasing the agitation.

IPTG was added in batch and fedbatch media when it was necessary at a final concentration of 20 μM. When it was needed, antibiotics were added at a concentration of 50 $mg \cdot L^{-1}$ for spectinomycin, 30 $mg \cdot L^{-1}$ for chloramphenicol, 50 $mg \cdot mL^{-1}$ for kanamycin and 100 $mg \cdot L^{-1}$ for ampicillin.

When the cell mass reached a concentration close to 5 $g \cdot L^{-1}$, the fedbatch was started with an initial flow rate of 5 $mL \cdot h^{-1}$. Feeding solution was injected with a sigmoid profile with an increasing flow rate that reached 24 $mL \cdot h^1$ after 25 hours. The precise feeding conditions were calculated by the equation:

$$Q(t) = p1 + \frac{p2}{1 + e^{-p3(t-p4)}}.$$

where Q(t) is the feeding flow rate in $mL \cdot h^1$ with p1=1.80, p2=22.4, p3=0.27, p4=6.50. This flow rate was increased from 10 to 50%, preferentially between 20 and 30% throughout the entire culture.

After 25 hours fedbatch, feeding solution pump was stopped and culture was finalized after glucose exhaustion.

Extracellular amino acids were quantified by HPLC after OPA/Fmoc derivatization and other relevant metabolites were analyzed using HPLC with refractometric detection (organic acids and glucose) and GC-MS after silylation.

Impact of the combination of metH, fldA, fpr overexpression and ygaZH overexpression in *E. coli* was tested. The results are presented in Table 8.

TABLE 8

Maximal and final methionine yields and homolanthionine concentrations produced in fedbatch cultures by the different strains.The performances of the strains of interest, strains 5, 6 and 7 are compared to the reference strain 1 and were cultivated in same conditions. The symbol ~ indicates that there is no difference between the strains, the symbol + indicates an increase between 1 to 5%, the symbol ++ indicates an increase between 5 to 10% and the symbol +++ indicates an increase greater than 10%. For the definition of methionine/glucose yield see below.

| Strain | Strain 1 | Strain 6 | Strain 5 | Strain 7 |
|---|---|---|---|---|
| Number of repetitions | n = 4 | n = 1 | n = 1 | n = 2 |
| Max methionine yield | reference | ~ | ++ | +++ |
| Final methionine yield | reference | ~ | ~ | ++ |
| Homolanthionine (mM) Concentration at the final point | 14.8 | ND | 3.6 | 2.5 |
| MetH Specific activity (mUI/mg of protein) | 230 | 230 | 1500 | ND |

These results show that in *E. coli*, the overexpression of ygaZH genes only is of no benefit to the production of methionine (strain 6). The overexexpression of the cobalamin-dependent methionine synthase system in *E. coli* (strain 5) leads to an improved production of methionine. Surprisingly, we observe that the combination of overexpression of the genes ygaZH and the cobalamin-dependent methionine synthase system has a synergistic effect on the methionine production leading to an unexpected increased production of methionine. Moreover this combination has also a favourable impact on the homolanthionine production leading to a methionine with better purity.

Determination of Methionine/Glucose Yield ($Y_{met}$)

The reactor volume was calculated by adding to the initial volume the amount of solutions added to regulate the pH and to feed the culture and by subtracting the volume used for sampling and lost by evaporation.

The fedbatch volume was followed continuously by weighing the feeding stock. The amount of injected glucose was then calculated on the basis of the injected weight, the density of the solution and the glucose concentration determined by the method of Brix ([Glucose]). The methionine yield was expressed as followed:

$$Y_{met} = \frac{Methionine_t * V_t * Methionine_0 * V_0 \times 100}{\text{Consumed } glucose_t}$$

With $Methionine_0$ and $Methionine_t$ respectively the initial and final methionine concentrations and $V_0$ and $V_t$ the initial and the instant t volumes.

The consumed glucose was calculated as follows:

$$fed\ volume_t = \frac{fed\ weight_0 - fed\ weight_t}{\text{density } fed \text{ solution}}$$

$$\text{Injected Glucose}_t = \text{fed volume}_t * [\text{Glucose}]$$

Consumed $glucose_t = [Glucose]_0 * V_0 +$ Injected Glucose $- [Glucose]_{residual} * V_t$ With $[Glucose]_0$, [Glucose], $[Glucose]_{residual}$ respectively the initial, the fed and the residual glucose concentrations.

Cobalamin-Dependent Methionine Synthase Activity Assay

The cobalamin-dependent methionine activity assay is an adaptation of the assay described by Drummond et al., in 1995.

The Cobalamin-dependent methionine synthase activity was assayed by measuring the product tetrahydrofolate (H4folate) concentration with a spectrophotometer at a wavelength of 350 nm and at a constant temperature of 37° C.

The reaction mixture was carried out in 80 mM potassium phosphate pH7.2, 20 mM DTT, 15 µM S-adenosylmethionine (SAM), 0.6 mM (6R,S)-5-Methyl-5,6,7,8-tetrahydrofolic acid, 40 µM Hydroxocobalamin, 0.1 mM Zinc chloride and 8 µg of crude extract in a final volume of 800 µl. The reaction mixture was incubated for 10 min at 37° C. before to start the reaction by the addition of the substrate homocysteine at a final concentration of 0.8 mM. After 5 min at 37° C., 200 µl of acidic derivatization solution (4M HCl in 60% formic acid) was added to quench the turnover bringing the volume to 1 ml, and the tubes are heated at 80° C. for 10 min. This step is necessary to stabilize the enzymatic product of the reaction, the tetrahydrofolate which is not stable in acid. The heat leads to the formation of the methenyltetrahydrofolate which absorbs light at 350 nm, while residual substrate 5-methyltetrahydrofolate does not contribute to the absorbance at 350 nm. The reaction blank contained all components of the reaction mixture except the substrate homocysteine.

Quantification of the FldA and Fpr Proteins Levels

In order to quantify the two proteins, antibodies were generated against the flavodoxin-1 (fldA) and the flavodoxin reductase (fpr) (Antibodies from rabbit, Eurogentec) and used in Western blot experiments. Western blot detection was carried out using goat anti-rabbit AP. The proteins levels of FldA and Fpr on stained blots were quantified with a commercially available imaging system (Epson Expression 1680 professional) and compared in the different strains described in this patent.

Example 6: Production of L-Methionine by Fermentation with *C. glutamicum* Strains Strains are cultivated in flask in the same conditions as described in patent application WO2009/144270.

TABLE 9

Methionine titers produced by *C. glutamicum* strains D, E, F, G and H compared to reference strain C.

| | Strain | | | | | |
|---|---|---|---|---|---|---|
| | Strain C | Strain F | Strain D | Strain E | Strain G | Strain H |
| Number of repetitions | n = 10 | n = 2 | n = 2 | n = 2 | n = 2 | n = 2 |
| Methionine Titer % compared to the strain | reference | ~ | + | ~ | ++ | + |

The symbol ~ indicates that there is no difference between the strains, the symbol + indicates an increase between 1 to 3%, the symbol ++ indicates an increase greater than 3%.

Similarly to *E. coli*, in *C. glutamicum*, the combination of overexpression of the genes brnFE and the cobalamin-dependent methionine synthase system (from *E. coli*—strain H and from *C. glutamicum*—strain G) has a synergistic effect on the methionine production leading to an unexpected increased production of methionine.

Example 7: Overproduction of the Cobalamin-Dependent Methionine Synthase and Overproduction of Homologous L-Methionine Secretion Systems in an *E. coli* Strain Overproducer of L-Methionine—Construction of Strains 8 to 17

The ygaZH homologous genes from *Citrobacter* species, *Raoultella* species, *Shigella* species, *Enterobacter* species, *Yersinia* species and *Photorhabdus* species were overexpressed in genetic background of strain 5.

Before using strain 5, the antibiotic cassette of the chromosomal integration made at ytfA locus was removed using the Flp recombinase as described by Datsenko & Wanner, 2000 (according to Protocol 1). The kanamycin sensible transformants were selected and the absence of antibiotic cassette at ytfA locus was verified by a PCR analysis with appropriate oligonucleotides. The resulting strain was named strain 8.

Construction of Strain 9—Overproduction of the Endogenous L-Methionine Secretion System, Overexpression of ygaZH from *E. coli*

To compare the effect of the overexpression of ygaZH from *E. coli* and overexpression of ygaZH homologues in the same genetic background, the plasmid pME1247 carrying ygaZH from *E. coli* was transformed into strain 8, giving rise to strain 9.

Construction of Strains 10 to 17—Overproduction of Homologous L-Methionine Secretion Systems, Overexpression of ygaZH from Genus and Species Listed in Table 10

To overexpress the ygaZH homologous genes listed in table 10, each couple of genes was cloned on the moderate copy number plasmid pCL1920 (Lerner & Inouye, 1990) with the use of the natural promoter and natural ribosome binding site of *E. coli* ygaZ gene as previously described for *E. coli* ygaZH genes, As specified in table 11, the ygaZH homologue genes were either amplified from genomic DNA of the corresponding strain or chemically synthesized, with or without optimizing the codon usage to *E. coli* (as proposed by GeneArt® Gene Synthesis service with GeneOptimizer® software—Lifetechnologies). The amplified DNA fragments comprising the ygaZH homologous genes are disclosed in SEQ ID indicated in the Table 11. The resulting plasmids were named as mentioned in table 11. Finally each plasmid was transformed into strain 8, giving the strains 10 to 17, as mentioned in table 11.

TABLE 10

YgaZH homologue proteins

| Organism | ygaZ Acession Number | ygaZ Name | ygaH Acession Number | ygaH Name |
|---|---|---|---|---|
| *Citrobacter koseri* | YP_001455539.1 NC_009792.1. ABV15103.1 | hypothetical protein CKO_04031 [*Citrobacter koseri* ATCC BAA-895] | YP_001455540.1 ABV15104.1 | hypothetical protein CKO_04032 [*Citrobacter koseri* ATCC BAA-895] |
| *Shigella flexneri* | WP_005122932.1 EIQ78635.1 | membrane protein [*Shigella flexneri*] | WP_005122930.1 EIQ78634.1 | branched-chain amino acid ABC transporter permease [*Shigella flexneri*] |
| *Raoultella ornithinolytica* | YP_007877063.1 AGJ89511.1 WP_015585890.1 | hypothetical protein RORB6_24155 [*Raoultella ornithinolytica* B6] | YP_007877062.1 AGJ89510.1 | L-valine exporter [*Raoultella ornithinolytica* B6] |
| *Enterobacter* sp. | YP_008107733.1 AGN85393.1 WP_020454909.1 | membrane protein [*Enterobacter* sp. R4-368] | YP_008107734.1 WP_020454910.1 AGN85394.1 | branched-chain amino acid ABC transporter permease [*Enterobacter* sp. R4-368] |
| *Yersinia enterocolitica* subsp. *Enterocolitica* | EKA28834.1 YWA314-01718 | putative amino acid transporter [*Yersinia enterocolitica* subsp. *enterocolitica* WA-314] | EKA288331 ou YWA314-01713 | hypothetical protein YE3239 [*Yersinia enterocolitica* subsp. *Enterocolitica* WA-314] |
| *Photorhabdus luminescens* subsp. *Laumondii* | NP_928590.1 CAE13573.1 | hypothetical protein plu1279 [*Photorhabdus luminescens* subsp. *laumondii* TTO1] | NP_928589.1 CAE13572.1 | hypothetical protein plu1278 [*Photorhabdus luminescens* subsp. *laumondii* TTO1] |
| *Citrobacter youngae* | WP_006687199.1 EFE06904.1 | membrane protein [*Citrobacter youngae*] putative azaleucine resistance protein AzlC [*Citrobacter youngae* ATCC 29220] | WP_006687198.1 EFE06903.1 | branched-chain amino acid ABC transporter permease [*Citrobacter youngae*] |
| *Citrobacter freundii* | WP_003839672.1 | hypothetical protein [*Citrobacter freundii*] | WP_003037297.1 | branched-chain amino acid ABC transporter permease [*Citrobacter freundii*] |

TABLE 11

Plasmids and strains carrying ygaZH homologue genes

| Microorganism | Chemical synthesis | Codon usage optimisation | SEQ ID N° | Plasmid name | Strain name |
|---|---|---|---|---|---|
| *Citrobacter koseri* | no | no | 28 | pME1277 | Strain 10 |
| *Shigella flexneri* | yes | no | 29 | pME1274 | Strain 11 |
| *Raoultella ornithinolytica* | yes | yes | 30 | pME1275 | Strain 12 |
| *Enterobacter* sp. | yes | yes | 31 | pME1283 | Strain 13 |

TABLE 11-continued

Plasmids and strains carrying ygaZH homologue genes

| Microorganism | Chemical synthesis | Codon usage optimisation | SEQ ID N° | Plasmid name | Strain name |
|---|---|---|---|---|---|
| *Yersinia enterocolitica* subsp. *Enterocolitica* | no | no | 32 | pME1287 | Strain 14 |
| *Photorhabdus luminescens* subsp. *Laumondii* | no | no | 33 | pME1281 | Strain 15 |

TABLE 11-continued

Plasmids and strains carrying ygaZH homologue genes

| Microorganism | Chemical synthesis | Codon usage optimisation | SEQ ID N° | Plasmid name | Strain name |
|---|---|---|---|---|---|
| Citrobacter youngae | yes | yes | 34 | pME1311 | Strain 16 |
| Citrobacter freundii | yes | yes | 35 | pME1307 | Strain 17 |

Example 8: Production of L-Methionine by Fermentation in Flask Experiments

Recombinant L-methionine producers overeproducing the cobalamin dependant methionine synthase MetH as well as different L-methionine secretion systems from various microorganisms (homologous to YgaZH from *E. coli*) were evaluated in small Erlenmeyer flasks.

Production strains were evaluated in small Erlenmeyer flasks. A 5.5 mL preculture was grown at 30° C. for 21 hours in a mixed medium (10% LB medium (Sigma 25%) with 2.5 g·L$^{-1}$ glucose and 90% minimal medium PC1). It was used to inoculate a 50 mL culture to an OD$_{600}$ of 0.2 in medium PC1. Spectinomycin was added at a concentration of 50 mg·L$^{-1}$ and gentamycin at 10 mg·L$^{-1}$ when it was necessary. The temperature of the cultures was 37° C. When the culture had reached an OD$_{600}$ of 5 to 7, extracellular amino acids were quantified by HPLC after OPA/Fmoc derivatization and other relevant metabolites were analyzed using HPLC with refractometric detection (organic acids and glucose) and GC-MS after silylation.

TABLE 12

Minimal medium composition (PC1)

| Compound | Concentration (g · L$^{-1}$) |
|---|---|
| ZnSO$_4$•7H$_2$O | 0.0040 |
| CuCl$_2$•2H$_2$O | 0.0020 |
| MnSO$_4$•H$_2$O | 0.0200 |
| CoCl$_2$•6H$_2$O | 0.0080 |
| H$_3$BO$_3$ | 0.0010 |
| Na$_2$MoO$_4$•2H$_2$O | 0.0004 |
| MgSO$_4$•7H$_2$O | 1.00 |
| Citric acid | 6.00 |
| CaCl$_2$•2H$_2$O | 0.04 |
| K$_2$HPO$_4$ | 8.00 |
| Na$_2$HPO$_4$ | 2.00 |
| (NH$_4$)$_2$HPO$_4$ | 8.00 |
| NH$_4$Cl | 0.13 |
| NaOH 4M | Adjusted to pH 6.8 |
| FeSO$_4$•7H$_2$O | 0.04 |
| Thiamine | 0.01 |
| Glucose | 20.00 |
| Ammonium thiosulfate | 5.61 |
| Vitamin B12 | 0.01 |
| MOPS | 20.00 |
| IPTG | 0.0048 |

TABLE 13

Methionine yield (Ymet) in g methionine/% g of glucose produced in flask culture by the strains of interest carrying overexpressions of ygaZH homologues genes as well as metH, fldA and fpr genes. For the precise definition of methionine/glucose yield see below. "n" indicates the number of repeats.

| Strain | Y$_{met}$ |
|---|---|
| Strain 8 (n = 2) | 16.0 |
| Strain 9 (*E. coli*) (n = 10) | 16.2 |
| Strain 10 (*C. koseri*) (n = 4) | 18.4 |
| Strain 11 (*S. flexneri*) (n = 1) | 16.6 |
| Strain 12 (*R. ornithinolytica*) (n = 2) | 16.2 |
| Strain 13 (*Enterobacter* sp.) (n = 2) | 18.8 |
| Strain 14 (*Y. enterocolitica* subsp. *Enterocolitica*) (n = 2) | 16.3 |
| Strain 15 (*P. luminescens* subsp. *Laumondii*) (n = 2) | 16.1 |
| Strain 16 (*C. youngae*) (n = 2) | 18.1 |
| Strain 17 (*C. freundii*) (n = 2) | 18.4 |

As can be seen in table 13, overexpression of ygaZH homologous genes from various microorganisms in the L-methionine producer overexpressing metH, fldA, fpr genes, leads to equivalent or better performances than those obtained with strain 9 which overexpresses ygaZH from *E. coli*. The homologous L-methionine secretion systems from other microorganisms than *E. coli* can replace the endogenous proteins of the bacterium.

The homologous proteins YgaZH from *Citrobacter Koseri* (strain 10, Ymet=19.6 g/g), *Citrobacter youngae* (strain 16, Ymet=19.6 g/g), *Citrobacter freundii* (strain 17, Ymet=19.6 g/g) and *Enterobacter* sp. (Strain 13, Ymet=19.4 g/g) showed the best L-methionine yields of production compared to strain 9 (Ymet=18.7 g/g).

The methionine yield was expressed as followed:

$$Y_{met} = \frac{\text{methionine (g)}}{\text{consummed glucose (g)}} * 100$$

REFERENCES

Anderson, 1946, *Proc. Natl. Acad. Sci. USA* 32:120-128.
Banerjee R. V., Harder S. R., Ragsdale S. W., Matthews R. G., 1990, *Biochemistry*, 29:1129-1135
Carrier T., Keasling J. D., 1999, *Biotechnology Progress*, 15:58-64
Datsenko K. A., Wanner B. L., 2000, *Proceedings of the National Academy of Sciences of the USA*, 97:6640-6645
Drummond J. T., Jarrett J., Gonzalez J. C., Huang S., Matthews R. G., 1995, *Analytical Biochemistry*, 228(2): 323-329.
Eikmanns B. J., Kleinertz E., Liebl W., Sahm H., 1991, *Gene*, 102:93-98
Foster M. A., Jones K. M., Woods D. D., 1961, *Biochemical Journal*, 80:519-531
Fujii K. and Huennekens F. M., 1974, *Journal of Biological Chemistry*, 249 (21):6745-6753

Gonzalez J. C., Banerjee R. V., Huang S., Summer J. S., Matthews R. G., 1992, *Biochemistry,* 31:6045-6056

Lerner C. G. and Inouye M., 1990, *Nucleic Acids Research,* 18(15):4631

Liebl et al., 1989, *Appl. Microbiol. Biotechnol.* 32: 205-210.

Matthews R. G., 2001, *Accounts of Chemical Research,* 34:681-689

Miller, 1992; *"A Short Course in Bacterial Genetics: A Laboratory Manual and Handbook for Escherichia coli and Related Bacteria"*, Cold Spring Harbor Laboratory Press, Cold Spring Harbor, N.Y.

Riedel et al., 2001, *J. Mol. Microbiol. Biotechnol.* 3: 573-583.

Saunderson C. L., 1985, *British Journal of Nutrition,* 54:621-633

Schaefer et al. 1999, *Anal. Biochem.* 270: 88-96.

Trötschel C., Deutenberg D., Bathe B., Burkovski A., Kramer R., 2005, *Journal of Bacteriology.* 187(11):3786-3794

Wan J. T. and Jarrett J. T., 2002, *Archives of Biochemistry and Biophysics,* 406:116-126

The invention claimed is:

1. A recombinant microorganism genetically modified to improve the production of methionine in comparison with an endogenous production of methionine in the corresponding wild-type microorganism, wherein said recombinant microorganism is recombinant *E. coli* and wherein in said recombinant microorganism, the expression of the *E. coli* metH, *E. coli* fldA and *E. coli* fpr genes is enhanced compared to the expression of said genes in the corresponding unmodified microorganism and the *E. coli* ygaZH genes, *Citrobacter* species ygaZH genes, *Shigella* species ygaZH genes, *Raoultella* species ygaZH genes, *Enterobacter* species ygaZH genes, *Yersinia* species ygaZH genes, or *Photorhabdus* species ygaZH genes are overexpressed compared to the expression of said genes in the corresponding unmodified microorganism, and wherein the enhanced expression and the overexpression are achieved by:

i) increasing the number of copies of the gene in the microorganism and/or ii) using a promoter leading to a high level of expression of the gene.

2. The recombinant microorganism of claim 1, wherein said *E. coli* metH, fldA and fpr genes are overexpressed chromosomally compared to the expression of said genes in the corresponding unmodified microorganism.

3. The recombinant microorganism of claim 1, wherein said *Citrobacter* species ygaZH genes, *Shigella* species ygaZH genes, *Raoultella* species ygaZH genes, *Entero-*

*bacter* species ygaZH genes, *Yersinia* species ygaZH genes, or *Photorhabdus* species ygaZH genes are *Citrobacter koseri* ygaZH genes, *Shigella flexneri* ygaZH genes, *Raoultella ornithinolytica* ygaZH genes, *Enterobacter* sp. ygaZH genes, *Yersinia enterocolitica* ygaZH genes, *Photorhabdus luminescens* ygaZH genes, *Citrobacter youngae* ygaZH genes, or *Citrobacter freundii* ygaZH genes.

4. The recombinant microorganism of claim 1, wherein said *E. coli* ygaZH genes, *Citrobacter* species ygaZH genes, *Shigella* species ygaZH genes, *Raoultella* species ygaZH genes, *Enterobacter* species ygaZH genes, *Yersinia* species ygaZH genes, or *Photorhabdus* species ygaZH genes are expressed under control of an inducible promoter.

5. The recombinant microorganism of claim 1, wherein the expression of at least one *E. coli* gene is also increased compared to the expression of said genes in the corresponding unmodified microorganism, wherein said at least one *E. coli* gene is selected from the group consisting of ptsG, pyc, pntAB, cysP, cysU, cysW, cysA, cysM, cysJ, cysI, cysH, gcvT, gcvH, gcvP, lpd, serA, serB, serC, cysE, metF, metA, metA* allele encoding for an enzyme with reduced feed-back sensitivity to S-adenosylmethionine and/or methionine, thrA, and a thrA* allele encoding for an enzyme with reduced feed-back inhibition to threonine, wherein said increased expression are achieved by:

i) increasing the number of copies of said genes and/or ii) using a promoter leading to a high level of expression of said genes.

6. The recombinant microorganism of claim 5, wherein at least one of said *E. coli* genes is under the control of an inducible promoter.

7. The recombinant microorganism of claim 1, wherein the expression of at least one *E. coli* gene is also attenuated, wherein said at least one *E. coli* gene is selected from the group consisting of metJ, pykA, pykF, purU, ybdL, yncA, metE, dgsA, metN, metI, metQ and udhA, compared to the expression of said genes in the corresponding unmodified microorganism, wherein said attenuation is achieved by mutations, deletions, and/or insertions in the promoter or coding regions of said genes.

8. The recombinant microorganism of claim 3, wherein:

a. the expression of the *E. coli* metA*, cysPUWAM, cysJIH, gcvTHP, metF, serA, serB, serC, cysE, thrA*, ptsG and pyc genes is enhanced compared to the expression of said genes in the corresponding unmodified microorganism, b. the expression of the *E. coli* metJ, pykA, pykF, purU, dgsA, metE and yncA genes is attenuated compared to the expression of said genes in the corresponding unmodified microorganism, c. said *E. coli* metH, fldA and fpr genes are overexpressed compared to the expression of said genes in the corresponding unmodified microorganism, and d. said *E. coli* ygaZ and ygaH genes, *Citrobacter koseri* ygaZ and ygaH genes, *Shigella flexneri* ygaZ and ygaH genes, *Raoultella ornithinolytica* ygaZ and ygaH genes, *Enterobacter* sp. ygaZ and ygaH genes, *Yersinia enterocolitica* ygaZ and ygaH genes, *Photorhabdus luminescens* ygaZ and ygaH genes, *Citrobacter youngae* ygaZ and ygaH genes, or *Citrobacter freundii* ygaZ and ygaH genes are overexpressed compared to the expression of said genes in the corresponding unmodified microorganism, wherein the enhanced expression and the overexpression are achieved by:

i) increasing the number of copies of the gene in the microorganism and/or ii) using a promoter leading to a high level of expression of the gene; and wherein said attenuation is achieved by mutations, deletions, and/or insertions in the promoter or coding regions of said genes.

9. A method for the fermentative production of methionine comprising:

a. culturing the recombinant microorganism as defined in claim 1 in an appropriate culture medium comprising a fermentable source of carbon and a source of sulphur, and b. recovering methionine from the culture medium.

* * * * *